(12) United States Patent
Breakefield et al.

(10) Patent No.: US 6,573,090 B1
(45) Date of Patent: Jun. 3, 2003

(54) ENHANCED PACKAGING OF HERPES VIRUS AMPLICONS AND GENERATION OF RECOMBINANT VIRUS VECTORS

(75) Inventors: Xandra O. Breakefield, Newton, MA (US); E. Antonio Chiocca, Brookline, MA (US); Yoshinaga Saeki, Takatsuki (JP); Cornel Fraefel, Wald (CH); Kurt Tobler, Chur (CH); Mathias Ackermann, Schwerzenbach (CH); Mark Suter, Lucerne (CH); Gosse J. Adema, Groesbeek (NL); Ken Shortman, Melbourne (AU)

(73) Assignees: The General Hospital Corporation, Boston, MA (US); University Medical Centre St. Radboud of the University of Nijmegen, Nijmegen (NL); University of Zurich, Zurich (CH); The Walter & Eliza Hall Institute of Medical Research, Partulla (AU)

( * ) Notice: Subject to any disclaimer, the term of this patent is extended or adjusted under 35 U.S.C. 154(b) by 0 days.

(21) Appl. No.: 09/458,068

(22) Filed: Dec. 9, 1999

Related U.S. Application Data

(60) Provisional application No. 60/161,374, filed on Oct. 26, 1999, and provisional application No. 60/111,630, filed on Dec. 9, 1998.

(51) Int. Cl.$^7$ .................. C12N 15/81; C12N 15/70; C12N 15/33; C12N 15/38; C12N 15/869
(52) U.S. Cl. ............... 435/320.1; 435/69.1; 435/6; 435/455.1; 435/375.1; 435/235.1; 435/239; 536/23.1; 514/44; 424/199.1; 424/201.1; 424/202.1; 424/203.1; 424/229.1; 424/234.1; 424/93.1
(58) Field of Search ............ 435/455, 6, 69.1, 435/375, 5, 320.1, 239, 235.1; 536/23.1; 514/44; 424/199.1, 201.1, 200.1, 202.1, 203.1, 229.1, 234.1, 93.2

(56) References Cited

U.S. PATENT DOCUMENTS

| | | | |
|---|---|---|---|
| 5,529,774 A | 6/1996 | Barba et al. | 424/93.21 |
| 5,601,818 A | 2/1997 | Freeman et al. | 424/93.21 |
| 5,631,236 A | 5/1997 | Woo et al. | 514/44 |
| 5,670,488 A | 9/1997 | Gregory et al. | 514/44 |
| 5,688,773 A | 11/1997 | Chiocca et al. | 514/44 |
| 5,691,177 A | 11/1997 | Guber et al. | 435/172.3 |
| 5,741,486 A | 4/1998 | Pathak et al. | 424/93.21 |
| 5,756,283 A | 5/1998 | Wilson et al. | 435/5 |
| 5,763,217 A | 6/1998 | Cynader et al. | 435/69.1 |
| 5,763,242 A | 6/1998 | Zhang et al. | 435/172.3 |
| 5,851,826 A * | 12/1998 | Fraefel et al. | 435/69.1 |
| 6,277,612 B1 * | 8/2001 | Golightly et al. | 435/320.1 |

FOREIGN PATENT DOCUMENTS

| | | |
|---|---|---|
| WO | WO 92/05263 | 4/1992 |
| WO | WO 95/06486 A1 | 3/1995 |
| WO | WO 97/05263 A1 | 2/1997 |
| WO | WO 99/43842 | 9/1999 |

OTHER PUBLICATIONS

Verma et al. Nature 1997, vol. 389, pp. 239–242.*
Orkin et al. 1996 Report and Recommendations of the Panel to Assess the NIH Investment in Research on Gene Therapy.*
Aboody–Guterman, K. S., et al., "Green fluorescent protein as a reporter for retrovirus and helper virus–free HSV–1 amplicon vector–mediated gene transfer into neural cells in culture and in vivo," *NeuroReport* 8:3801–3808 (Dec. 1997).
Ace, C. I., et al., "Construction and Characterization of a Herpes Simplex Virus Type 1 Mutant Unable to Transinduce Immediate–Early Gene Expression," *J. Virol.* 63:2260–2269 (1989).
Bergold, P. J., et al., "Transsynaptic neuronal loss induced in hippocampal slice cultures by a herpes simplex virus vector expressing the GluR6 subunit of the kainate receptor," *Proc. Natl. Acad. Sci. USA* 90:6165–6169 (1993).
Bilbao, G., et al., "Adenoviral/retroviral vector chimeras: a novel strategy to achieve high–efficiency stable transduction in vivo," *FASEB J.* 11:624–634 (Jul. 1997).
Breakfield, X. O., et al., "Herpes Simplex Virus Vectors for Tumor Therapy," in *The Internet Book of Gene Therapy, Cancer Therapeutics*, Sobel, R. E. and Scanlon, K. J., eds., Appleton & Lange, Stanford, CT, pp. 41–56 (1995).
Chase, M., et al., "An oncolytic viral mutant that delivers the CYP2B1 transgene and augments cyclophosphamide chemotherapy," *Nature Biotechnol.* 16:444–448 (May 1998).
Cose, S. C., et al., "Characterization of a Diverse Primary Herpes Simplex Virus Type 1 gB–Specific Cytotoxic T–Cell Response Showing a Preferential Vβ Bias," *J. Virol.* 69:5849–5852 (1995).

(List continued on next page.)

*Primary Examiner*—James Housel
*Assistant Examiner*—Bao Qun Li
(74) *Attorney, Agent, or Firm*—Sterne, Kessler, Goldstein & Fox P.L.L.C.

(57) ABSTRACT

The present invention relates to an enhanced and simplified herpes virus amplicon packaging system. The packaging system comprises a herpes virus amplicon vector and a packaging vector. In one embodiment, the packaging vector comprises a bacterial artificial chromosome (BAC) containing the HSV-1 genome. The packaging vector contains an intact pac site but is otherwise rendered packaging defective. The packaging vector can be rendered packaging defective by inserting nucleotides into the pac site, or by otherwise interfering with the capsid's ability to close, for example, by increasing the size of the DNA fragment upon which the herpes virus genome is cloned. This system can be used to package a wide range of nucleotide sequences (e.g., a therapeutic or antigenic gene) into an empty herpes virus particle taking advantage of the large transgene capacity of herpes viruses. This system can also be used as a vaccine to induce protective immunity against HSV-1, or other complex pathogens.

29 Claims, 12 Drawing Sheets

OTHER PUBLICATIONS

Cose, S. C., et al., "Antigen–specific CD8+ T cell subset distribution in lymph nodes draining the site of herpes simplex virus infection," *Eur. J. Immunol.* 27:2310–2316 (Sep. 1997).

Coulter, L. J., et al., "A mutant of herpes simplex virus type 1 in which the UL13 protein kinase gene is disrupted," *J. Gen. Virol.* 74:387–395 (1993).

Cunningham, C., et al., "The UL13 virion protein of herpes simplex virus type 1 is phosphorylated by a novel virus–induced protein kinase," *J. Gen. Virol.* 73:303–311 (1992).

Cunningham, C., and Davison, A. J., "A Cosmid–Based System for Contructing Mutants of Herpes Simplex Virus Type 1," *Virol.* 197:116–124 (1993).

Delecluse, H.–J., et al., "Propagation and recovery of intact, infectious Epstein–Barr virus from prokaryotic to human cells," *Proc. Natl. Acad. Sci. USA* 95:8245–8250 (Jul. 1998).

Dornburg, R., "Reticuloendotheliosis viruses and derived vectors," *Gene Therapy* 2:301–310 (1995).

Evans, G. A., et al., "High efficiency vectors for cosmid microcloning and genomic analysis," *Gene* 79:9–20 (1989).

Ferrin, L. J., and Camerini–Otero, R. D., "Selective Cleavage of Human DNA: RecA–Assisted Restriction Endonuclease (RARE) Cleavage," *Science* 254:1494–1497 (1991).

Flotte, T. R., and Carter, B. J., "Adeno–associated virus vectors for gene therapy," *Gene Therapy* 2:357–362 (1995).

Forss–Petter, S., et al., "Neuron–Specific Enolase: Complete Structure of Rat mRNA, Multiple Transcriptional Start Sites, and Evidence Suggesting Post–Transcriptional Control," *J. Neuroscience Res.* 16:141–156 (1986).

Fraefel, C., et al., "Helper Virus–Free Transfer of Herpes Simplex Virus Type 1 Plasmid Vectors into Neural Cells," *J. Virol.* 70:7190–7197 (Oct. 1996).

Fraefel, C., et al., "Gene Transfer into Hepatocytes Mediated by Helper Virus–Free HSV/AAV Hybrid Vectors," *Mol. Med.* 3:813–825 (Dec. 1997).

Fraefel, C., et al., "HSV–1 Amplicon," in *Gene Therapy for Neurological Disorders and Brain Tumors*, Chiocca, E. A. and Breakefield, X. O., eds., Humana Press Inc., Totowa, NJ., pp. 63–82 (Oct. 1998).

Fraefel, C., "Gene Delivery Using Helper Virus–Free HSV–1 Amplicon Vectors," in *Current Protocols in Neuroscience*, vol. 1, Crawley, J.N. et al., eds., John Wiley & Sons, Inc., New York, NY, pp. 4.14.1–4.14.15 (1999).

Geller, A. I., et al., "An efficient deletion mutant packaging system for defective herpes simplex virus vectors: Potential applications to human gene therapy and neuronal physiology," *Proc. Natl. Acad. Sci. USA* 87:8950–8954 (1990).

Glorioso, J. C., et al., "Herpes Simplex Virus as a Gene–Delivery Vector for the Central Nervous System," in *Viral Vectors*, Academic Press, Inc., San Diego, CA, pp. 1–23 (1995).

Ioannou, P. A., et al., "A new bacteriophage P1–derived vector for the propagation of large human DNA fragments," *Nature Genetics* 6:84–89 (1994).

Jennings, S. R., et al., "CD4–Positive T Lymphocytes Are Required for the Generation of the Primary but Not the Secondary CD8–Positive Cytolytic T Lymphocyte Response to Herpes Simplex Virus in C57BL/6 Mice," *Cell. Immunol.* 133:234–252 (1991).

Johnston, K. M., et al., "HSV/AAV Hybrid Amplicon Vectors Extend Transgene Expression in Human Glioma Cells," *Human Gene Ther.* 8:359–370 (Feb. 1997).

Jones, C. M., et al., "Evidence for cooperation between TCR V region and junctional sequences in determining a dominant cytotoxic T lymphocyte response to herpes simplex virus glycoprotein B," *International Immunol.* 9:1319–1328 (Sep. 1997).

Kilby, N. J., et al., "Site–specific recombinases: tools for genome engineering," *Trends in Genetics* 9:413–421 (1993).

Knuchel, M., et al., "An ELISA for detection of antibodies against porcine epidemic diarrhoea virus (PEDV) based on the specific solubility of the viral surface glycoprotein," *Veterinary Microbiol.* 32:117–134 (1992).

Kramm, C. M., et al., "Gene Therapy for Brain Tumors," *Brain Pathology* 5:345–381 (1995).

Latchman, D. S., "Herpes Simplex Virus Vectors for Gene Therapy," *Mol. Biotech.* 2:179–195 (1994).

Lim, F., et al., "Generation of High–Titer Defective HSV–1 Vectors Using an IE 2 Deletion Mutant and Quantitative Study of Expression in Cultured Cortical Cells," *BioTechniques* 20:460–469 (Mar. 1996).

Lopez, C., et al., "Immunity to Herpesvirus Infections in Humans," in *The Human Herpesviruses*, Roizman, B., et al., eds., Raven Press, Ltd., New York, NY, pp. 397–425 (1993).

Luckow, V. A., et al., "Efficient Generation of Infectious Recombinant Baculoviruses by Site–Specific Transposon–Mediated Insertion of Foreign Genes into a Baculovirus Genome Propagated in *Escherichia coli*," *J. Virol.* 67:4566–4579 (1993).

McGeoch, D. J., et al., "The Complete DNA Sequence of the Long Unique Region in the Genome of Herpes Simplex Virus Type 1," *J. Gen. Virol.* 69:1531–1574 (1988).

Meignier, B., et al., "Virulence of and Establishment of Latency by Genetically Engineered Deletion Mutants of Herpes Simplex Virus 1," *Virol.* 162:251–254 (1988).

Messerle, M., et al., "Cloning and mutagenesis of a herpesvirus genome as an infectious bacterial artificial chromosome," *Proc. Natl. Acad. Sci. USA* 94:14759–14763 (Dec. 1997).

Nakanishi, M., "Gene Introduction Into Animal Tissues," *Crit. Rev. Ther. Drug Carrier Sys.* 12:263–310 (1995).

O'Connor, M., et al., "Construction of Large DNA Segments in *Escherichia coli*," *Science* 244:1307–1312 (1989).

Pertmer, T. M., et al., "Gene gun–based nucleic acid immunization: elicitation of humoral and cytotoxic T lymphocyte responses following epidermal delivery of nanogram quantities of DNA," *Vaccine* 13:1427–1430 (1995).

Posavad, C. M., et al., "Tipping the scales of herpes simplex virus reactivation: The important responses are local," *Nature Med.* 4:381–382 (Apr. 1998).

Read, G. S., et al., "Isolation of a Herpes Simplex Virus Type 1 Mutant with a Deletion in the Virion Host Shutoff Gene and Identification of Multiple Forms of the vhs (UL41) Polypeptide," *J. Virol.* 67:7149–7160 (1993).

Robbins, P. D., et al., "Viral vectors for gene therapy," *TIBTECH* 16:35–40 (Jan. 1998).

Rösen–Wolff, A., et al., "Elimination of UL56 gene by insertion of LacZ cassette between nucleotide position 116030 to 121753 of the herpes simplex virus type 1 genome abrogates intraperitoneal pathogenicity in tree shrews and mice," *Virus Res.* 20:205–221 (1991).

Saeki, Y., et al., "Herpes Simplex Virus Type 1 DNA Amplified as Bacterial Artificial Chromosome in *Escherichia coli*: Rescue of Replication–Competent Virus Progeny and Packaging of Amplicon Vectors," *Human Gene Therapy* 9:2787–2794 (Dec. 1998).

Salvucci, L. A., et al., "Polymorphism within the Herpes Simplex Virus (HSV) Ribonucleotide Reductase Large Subunit (ICP6) Confers Type Specificity for Recognition by HSV Type 1–Specific Cytotoxic T Lymphocytes," *J. Virol.* 69:1122–1131 (1995).

Shaughnessy, E., et al., "Parvoviral Vectors for the Gene Therapy of Cancer," *Seminars in Oncol.* 23:159–171 (Feb. 1996).

Shizuya, H., et al., "Cloning and stable maintenance of 300–kilobase–pair fragments of human DNA in *Escherichia coli* using an F–factor–based vector," *Proc. Natl. Acad. Sci. USA* 89:8794–8797 (1992).

Siegrist, C.– A., et al., "Induction of neonatal TH1 and CTL responses by live viral vaccines: a role for replication patterns within antigen presenting cells?" *Vaccine* 16:1473–1478 (Aug./Sep. 1998).

Smith, P. M., et al., "Control of Acute Cutaneous Herpes Simplex Virus Infection: T Cell–Mediated Viral Clearance Is Dependent upon Interferon–γ (IFN–γ)," *Virol.* 202:76–88 (1994).

Song, S., et al., "An HSV–1 Vector Containing the Rat Tyrosine Hydroxylase Promoter Enhances Both Long–Term and Cell Type–Specific Expression in the Midbrain," *J. Neurochem.* 68:1792–1803 (May 1997).

Spaete, R. R., and Frenkel, N., "The Herpes Simplex Virus Amplicon: A New Eucaryotic Defective–Virus Cloning–Amplifying Vector," *Cell* 30:295–304 (1982).

Stavropoulos, T. A., and Strathdee, C. A., "An Enhanced Packaging System for Helper–Dependent Herpes Simplex Virus Vectors," *J. Virol.* 72:7137–7143 (Sep. 1998).

Suter, M., et al., "BAC–VAC, a novel generation of (DNA) vaccines: A bacterial artificial chromosome (BAC) containing a replication–competent, packaging–defective virus genome induces protective immunity against herpes simplex virus 1," *Proc. Natl. Acad. Sci. USA* 96:12697–12702 (Oct. 1999).

Valyi–Nagy, T., et al., "Herpes Simplex Virus Type 1 Murtant Strain in1814 Establishes a Unique, Slowly Progressing Infection in SCID Mice," *J. Virol.* 66:7336–7345 (1992).

Vasilakos, J. P., and Michael, J. G., "Herpes Simplex Virus Class I–Restricted Peptide Induces Cytotoxic T Lymphocytes In Vivo Independent of CD4+ T Cells," *J. Immunol.* 150:2346–2355 (1993).

Watson, J. D., et al., "Chapter 28: Working Toward Human Gene Therapy," in *Recombinant DNA*. 2nd Ed., W. H. Freeman & Co., New York, NY, pp. 567–581 (1992).

Willetts, N., and Skurray, R., "64. Structure and Function of the F Factor and Mechanism of Conjugation," in *Eschericia Coli & Salmonella Typhimurium, Cellular and Molecular Biology*, vol. 2, American Society for Microbiology, Washington, DC, pp. 1110–1113 (1987).

Wolfe, J. H., et al., "Herpesvirus vector gene transfer and expression of β–glucuronidase in the central nervous system of MPS VII mice," *Nature Genetics* 1:379–384 (1992).

Yang, X. W., et al., "Homologous recombination based modification in *Escherichia* [sic] *coli* and germline transmission in transgenic mice of a bacterial artificial chromosome," *Nature Biotechnol.* 15:859–865 (Sep. 1997).

Zhang, Y. and Russell, S.J., "Vectors for cancer gene therapy," *Cancer & Metastasis Reviews* 15:385–401 (1996).

Zhang, Y., et al., "A new logic for DNA engineering using recombination in *Escherichia coli*," *Nature Genetics* 20:123–128 (Oct. 1998).

* cited by examiner

SEQUENCE LISTING

```
<160> NUMBER OF SEQ ID NOS: 2

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      Oligonucleotide

<400> SEQUENCE: 1
tcgagggccc ttaattaaga tcttaattaa gggccc                              36

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Ser Ser Ile Glu Phe Ala Arg Leu
  1               5
```

ENHANCED PACKAGING OF HERPES VIRUS AMPLICONS AND GENERATION OF RECOMBINANT VIRUS VECTORS

CROSS-REFERENCES TO RELATED APPLICATIONS

This application claims the benefit of U.S. Provisional Application No. 60/111,630, filed Dec. 9, 1998, and U.S. Provisional Application No. 60/161,374, filed Oct. 26, 1999. The content of all the aforesaid applications are relied upon and incorporated by reference in their entirety.

STATEMENT AS TO RIGHTS TO INVENTIONS MADE UNDER FEDERALLY-SPONSORED RESEARCH AND DEVELOPMENT

The U.S. Government has a paid-up license in this invention and the right in limited circumstances to require the patent owner to license others on reasonable terms as provided for by the terms of grant numbers NINDS NS24279 and NCI P01 CA69246, awarded by the National Institutes of Health.

BACKGROUND OF THE INVENTION

1. Field of the Invention

The present invention relates to herpes virus viral vectors. More specifically, the present invention relates to a novel method to package amplicon vectors and to generate recombinant virus vectors, and in particular herpes simplex virus type I (HSV-1) vectors, for use in gene transfer, gene therapy, and DNA-based vaccination strategies.

2. Related Art

The terms "gene transfer" and "gene therapy" have been used to describe a variety of methods for delivering genetic material to a cell using viral or non-viral based vector systems. Substantial attention has been given to human gene therapy. The transfer of genetic material to a cell may one day become one of the most important forms of medicine. A variety of public and private institutions now participate in research and development related to the use of genetic material in therapeutic applications. Hundreds of human gene transfer protocols are being conducted at any given time with the approval of the Recombinant DNA Advisory Committee (RAC) and the National Institutes of Health (NIH). Most of these protocols focus on therapy, while others involve marking and non-therapeutic applications. The therapeutic protocols are primarily concerned with infectious diseases, monogenic diseases, and cancer. Gene-based therapies are now expanding into fields such as cardiovascular disease, autoimmune disease, and neurodegenerative disease. The availability of an efficient gene delivery and expression system is essential to the success and efficacy of gene-based therapy.

One method of delivering a gene of interest to a target cell of interest is by using a viral-based vector. Techniques for the formation of vectors or virions are generally described in "Working Toward Human Gene Therapy," Chapter 28 in *Recombinant DNA*, 2nd Ed., Watson, J. D. et al., eds., New York: Scientific American Books, pp. 567–581 (1992). An overview of viral vectors or virions that have been used in gene therapy can be found in Wilson, J. M., *Clin. Exp. Immunol.* 107(Suppl. 1):31–32 (1997), as well as Nakanishi, M, *Crit. Rev. Therapeu. Drug Carrier Systems* 12:263–310 (1995); Robbins, P. D., et al., *Trends Biotechnol.* 16:35–40 (1998); Zhang, J., et al., *Cancer Metastasis Rev.* 15:385–401 (1996); and Kramm, C. M., et al., *Brain Pathology* 5:345–381 (1995). Such vectors may be derived from viruses that contain RNA (Vile, R. G., et al., *Br. Med Bull.* 51:12–30 (1995)) or DNA (Ali M., et al., *Gene Ther.* 1:367–384 (1994)).

Specific examples of viral vector systems that have been utilized in the gene therapy art include: retroviruses (Vile, R. G., supra; U.S. Pat. Nos. 5,741,486 and 5,763,242); adenoviruses (Brody, S. L., et al., *Ann. N.Y. Acad. Sci.* 716: 90–101 (1994); Heise, C. et al., *Nat. Med.* 3:639–645 (1997)); adenoviral/retroviral chimeras (Bilbao, G., et al., *FASEB J.* 11:624–634 (1997); Feng, M., et al., *Nat. Biotechnol.* 15:866–870 (1997)); adeno-associated viruses (Flotte, T. R. and Carter, B. J., *Gene Ther.* 2:357–362 (1995); U.S. Pat. No. 5,756,283); herpes simplex virus I or II (Latchman, D. S., *Mol. Biotechnol.* 2:179–195 (1994); U.S. Pat. No. 5,763,217; Chase, M., et al., *Nature Biotechnol.* 16:444–448 (1998)); parvovirus (Shaughnessy, E., et al., *Semin Oncol.* 23:159–171 (1996)); reticuloendotheliosis virus (Donburg, R., *Gene Therap.* 2:301–310 (1995)). Other viruses that can be used as vectors for gene delivery include poliovirus, papillomavirus, vaccinia virus, lentivirus, as well as hybrid or chimeric vectors incorporating favorable aspects of two or more viruses (Nakanishi, M, *Crit. Rev. Therapeu. Drug Carrier Systems* 12:263–310 (1995); Zhang, J., et al., *Cancer Metastasis Rev.* 15:385–401 (1996); Jacoby, D. R., et al., *Gene Therapy* 4:1281–1283 (1997)). Guidance in the construction of gene therapy vectors and the introduction thereof into affected animals for therapeutic purposes may be obtained in the above-referenced publications, as well as U.S. Pat. Nos. 5,631,236, 5,688,773, 5,691,177, 5,670,488, 5,529,774, 5,601,818, and WO 95/06486.

The viral vectors mentioned above have advantages and disadvantages. For example, retroviruses have the ability to infect cells and have their genetic material integrated into the host cell with high efficiency. The development of a helper virus free packaging system for retrovirus vectors was a key innovation in the development of this vector system for human gene therapy. Retroviral helper virus free packaging systems generally employ the creation of a stable producer cell line that expresses a selected vector. The relatively small size of the retroviral genome, approximately 11 kb, and the ability to express viral genes without killing cells, allows for the production of a packaging cell line that synthesizes all the proteins required for viral assembly. Producer lines are made by introducing the retroviral vector into such a packaging cell line.

On a down side, however, numerous difficulties with retroviruses have been reported. For example, most retroviral vectors are not capable of gene transfer to postmitotic (nondividing) cells and are thus not applicable to the nervous system because most of the cells in the adult nervous system, especially neurons, are quiescent or postmitotic. In addition, outbreaks of wild-type virus from recombinant virus-producing cell lines have also been reported with the vector itself causing a disease.

Difficulties have been noted with other viral vectors as well. Adenovirus vectors can only support limited long-term (2 months) gene expression, they appear to be gradually lost from neural cells, and moreover, they can cause both cytopathic effects and an immune response (Le Gal La Salle, G., et al., *Science* 259:988–990 (1993); Davidson et al., *Nat. Genet.* 3:219–223 (1993); Yang, Y., et al., *J. Virol.* 69:2004–2015 (1995)). Adeno-associated virus vectors cause minimal cytopathic effects and can support at least some gene expression for up to 4 months, but gene transfer is inefficient and these vectors can accept only ~4 kb of foreign DNA (Kaplitt, M. G., et al., *Nat. Genet.* 8:148–154 (1994)).

Vectors based on herpes simplex virus (HSV), and especially HSV-1, have shown considerable promise as potent gene delivery vehicles for several reasons: the virus has a very large genome and thus can accommodate large amounts of foreign DNA (greater than 30 kb), the virus can persist long-term in cells, and can efficiently infect many different cell types, including post-mitotic neural cells (Breakefield, X. O., et al., "Herpes Simplex Virus Vectors for Tumor Therapy," in *The Internet Book of Gene Therapy: Cancer Gene Therapeutics*, R. E. Sobol and K. J. Scanlon, eds. Appleton and Lange, Stamford, Conn., pp. 41–56 (1995); Glorioso, J. C., et al., "Herpes Simplex Virus as a Gene-Delivery Vector for the Central Nervous System," in Viral Vectors: *Gene Therapy and Neuroscience Applications*, M. G. Kaplitt and A. D. Loewy, eds., Academic Press, New York, pp. 1–23 (1995)).

There are two types of HSV-1 vector systems: recombinant and amplicon. Recombinant HSV-1 vectors (Wolfe, J. H. et al., *Nat. Genet.* 1:379–384 (1992)) are created by inserting genes of interest directly into the ~152 kb virus genome, thereby mutating one or more of the ~80 virus genes and concomitantly reducing cytotoxicity. In contrast, HSV-1 amplicons are bacterial plasmids containing only ~1% of the 152 kb HSV-1 genome, that are packaged into HSV-1 particles (virions) using HSV-1 helper virus. HSV-1 amplicons contain: (i) a transgene cassette with the gene of interest; (ii) sequences that allow plasmid propagation in *E. coli*, such as the origin of DNA replication colE1 and the ampicillin resistance gene; and (iii) non-coding elements of the HSV-1 genome, in particular an origin of DNA replication (ori) and a DNA cleavage/packaging signal (pac), to support replication and subsequent packaging of the amplicon DNA into virions in the presence of helper functions (Spaete, R. R. and Frenkel, N., *Cell* 30:295–304 (1982)). HSV amplicon vectors are one of the most versatile, most efficient, and least toxic, and have the largest transgene capacity of the currently available virus vectors. HSV-1 amplicon vectors can support some gene expression for up to one year (During, M. J., et al., *Science* 266:1399–1403 (1994)).

Because HSV-1 encodes many toxic functions, improvements on the amplicon system have been targeted primarily at reducing the risk associated with the helper virus. First, replication-competent HSV-1, initially used as helper virus, was replaced by a temperature-sensitive (ts) mutant of HSV-1 (HSV-1 tsK; Preston, C., *J. Virol.* 29:257–284 (1979)). This mutant encodes a temperature-sensitive form of the essential HSV-1 infected cell protein (ICP) 4, allowing HSV-1 replication to proceed at 31° C., but not at 37° C. Amplicons packaged at 31° C. in the presence of HSV-1 tsK were successfully used to transfer the *E. coli* lacZ gene into primary cultures of rat neural cells (Geller, A. I. and Breakefield, X. O., *Science* 241:1667–1669 (1988)). Because the infection was performed at 37° C., the lytic cycle of the HSV-1 tsK helper virus present in the vector stock was blocked and cell damage was limited. Although replication of HSV-1 tsK was inhibited at the restrictive temperature, the expression of other viral genes caused cytopathic effects. Moreover, reversion to wild type (wt) HSV-1 occurred at a relatively high frequency, due to remaining functionality and reversion of the point mutation in tsICP4.

To counter these problems, replication-defective mutants of HSV-1 were then used as helper viruses (Geller, A. I. et al., *Proc. Natl. Acad. Sci. USA* 87:8950–8954 (1990); Lim, F., et al., *BioTechniques* 20:458–469 (1996)). These mutants carry deletions in genes that are essential for virus replication, but they can support amplicon packaging in cells that complement the missing functions. In general, deletion-mutant packaging systems produce relatively high amplicon vector titers ($10^6$–$10^7$ transducing units per ml (t.u./ml)), a ratio of transducing vector units to helper virus of up to 1, and low levels of revertants with wt HSV-1 phenotype ($<10^{-7}$ plaque forming units (PFU), per ml; Lim, F., et al., supra). However, many problems associated with the presence of helper virus in amplicon stocks still remained, including: (i) pronounced cytopathic effects and immune responses caused by gene expression from the helper virus; (ii) interactions between the helper virus and endogenous viruses; (iii) reversion of the helper virus to wt HSV-1; and (iv) disregulation of transgene expression by virus proteins.

Many of these problems have been overcome by the more recent development of a packaging system for herpes virus vectors that was free of helper virus (Fraefel, C., et al., *J. Virol.* 70:7190–7197 (1996); International Patent Publication WO 97/05263, published Feb. 13, 1997)). This system utilizes transient co-transfection of amplicon DNA with a set of five cosmids that overlap and represent the entire HSV-1 genome, but which are mutated to delete the DNA cleavage/packaging (pac) signals. Cunningham, C. and Davison, A. J., *Virology* 197:116–124 (1993), had demonstrated previously that after transfection into cells, an overlapping HSV-1 cosmid set can produce infectious virus progeny. By deleting the pac signals and making a pac-minus helper virus genome, HSV-1 genomes that are potentially reconstituted from the cosmids via homologous recombination, are not packageable, but can still provide all the helper functions required for the replication and packaging of the co-transfected amplicon DNA. The resulting vector stocks are, therefore, virtually free of detectable helper virus and have titers of $10^6$–$10^7$ t.u./ml of culture medium. Because of minimal sequence homology between the cosmids and the amplicon DNA ($ori_s$; 0.2–1 kb), the formation of a packageable and replication-competent HSV-1 genome is possible but requires 6 recombination events, and is therefore very rare. Amplicon vector stocks, produced by using the helper virus-free packaging system, can efficiently transduce many different cell types, including neural cells and hepatocytes in culture and in vivo, while causing minimal to no cytopathic effects (Fraefel, C., et al.,*J. Virol.* 70:7190–7197 (1996); Fraefel, C., et al., *Mol. Med.* 3:813–825 (1997); Fraefel, C., et al., "HSV-1 Amplicon" in *Gene Therapy for Neurological Disorders and Brain Tumors*, E. A. Chiocca and X. O. Breakefield, eds., Humana Press, Totowa, pp. 63–82 (1998); Johnston, K. M., et al., *Hum. Gene Ther.* 8:359–370 (1997); Aboody-Guterman, K. S., et al., *NeuroReport* 8:3801–3808 (1997)).

Although the production of vector particles in the above mentioned system requires the cells to be simultaneously co-transfected with all five clones of the cosmid set and the amplicon DNA, thus making the system technically demanding to use, the titers of the resulting amplicon stocks are surprisingly high and comparable to those achieved with the helper virus-dependent systems.

Nevertheless, there is a need in the art to simplify and enhance this packaging system. By reducing the number of clones representing the HSV-1 genome to a single clone, the present inventors' hypothesized that it would be possible to further increase the packaging efficiency and increase the titer of the amplicon vector stocks.

SUMMARY OF THE INVENTION

The inventors have now discovered an improved and simplified herpesvirus amplicon packaging system.

Preferably, the herpesvirus is an alpha herpesvirus such as herpes simplex virus (HSV-1 or HSV-2), Varicella-Zoster virus, or pseudorabies virus. HSV-1 is particularly preferred. Other preferred herpesviruses are the Epstein-Barr virus (EBV) and the cytomegalovirus (CMV).

In a preferred embodiment, the complete 152 kb HSV-1 genome was cloned, both with and without a pac signal, and stably maintained as a single-copy, F-plasmid based bacterial artificial chromosome (BAC) in *E. coli*. When cloned with a pac signal in BAC (i.e., pac+), the pac signal was either outside the HSV-1 genome per se, or in the HSV-1 genome within the BAC. Having the pac sequence outside the HSV-1 genome is particularly preferred. Thus, contrary to the method of Fraefel et al., *J. Virol.* 70:7190–7197(1996), supra, (which utilized a set of 5 overlapping HSV-1 cosmid clones to encode the complete HSV-1 genome, and from which the packaging or pac elements were deleted), the entire packaging defective HSV-1 genome was cloned as a single plasmid DNA by using a BAC cloning vector. This system can then be used to package a wide range of desired nucleotide segments, preferably a DNA segment, into an empty herpesvirus particle (i.e., an HSV amplicon vector) taking advantage of the large transgene capacity of herpesviruses. Recombinant HSV-1 vectors can also be generated by recombination of BAC in bacteria or in mammalian cells using the "pac-rescue" technique. This technique involves targeted recombination of modified HSV-1 sequences bearing the pac sequence into a pac minus HSV BAC construct, with "rescue" of the pac plus modified genome by transfection and propagation in permissive mammalian cells.

Accordingly, the present invention overcomes the disadvantages of the prior art by providing a system for packaging herpesvirus amplicon vectors into infectious particles that are substantially free of helper virus contamination by using as a helper virus a packaging vector comprising a single clone, and in particular a bacterial artificial chromosome (BAC), containing the entire HSV-1 genome, said single clone being replication proficient but packaging defective. Thus, in a preferred embodiment, the herpesvirus amplicon can be packaged into infectious particles by cotransfection with a single HSV-BAC packaging vector in permissive mammalian cells, with the resulting amplicon stocks being free of helper virus contamination, yet high in vector titer. The packaging vector provides helper virus functions, such as replicative and virion assembly functions.

The present method for packaging a herpesvirus particle is based upon using a single packaging vector, such as a BAC, which upon delivery into a cell capable of supporting herpesvirus replication will form a DNA segment (or segments) capable of expressing sufficient structural herpesvirus proteins to replicate viral DNA and generate virions. BACs are based on the single-copy F-plasmid of *E. coli* and have been demonstrated previously to stably maintain human genomic DNA of >300 kb, and genomes of large DNA viruses, including those of baculovirus and murine cytomegalovirus (Shizuya, H., et al., *Proc. Natl. Acad. Sci. USA* 89:8794–8797 (1992); Luckow, V. A., et al., *J. Virol.* 67:4566–4579 (1993); Messerle, M., et al., *Proc. Natl. Acad Sci. USA* 94:14759–14763 (1997)). Although a BAC vector is particularly preferred, other large capacity cloning vectors known to those skilled in the art can also be used in the present invention.

In one embodiment of the above method, the packaging vector (i.e., BAC) is made packaging defective by deleting the herpesvirus cleavage-packaging site containing sequence (pac) entirely or by deleting a sufficient portion to render it incapable of packaging. Alternatively, another strategy is to insert nucleotides into such a site to render it non-functional. The pac sequence can be deleted from the packaging vector by any of a variety of techniques well known to the person of ordinary skill in the art.

In yet another embodiment of the present invention, the packaging vector is made packaging defective by rendering the HSV-1 genome unable to be packaged, even though it bears the pac sequence. That is, the packaging vector contains a pac sequence, however, the viral genome is on a DNA fragment that, due to its size, is unable to be packaged into viable HSV particles. For example, when the DNA fragment is too large, the helper virus HSV-1 genome in the packaging vector enters the capsid, but the capsid cannot close to generate infectious virus.

In order to understand this embodiment, it is important to understand the way the virus genome is packaged. The virus genome is replicated as a concatenate; it attaches to the open site on the incomplete virus capsid via a terminal pac sequence. The virus DNA is then threaded into the capsid until it is full, with a capacity of about 150 kb. At this point in the normal virus sequence there is another pac site and the DNA is cleaved at this point with subsequent closure of the virus capsid. This process has two important correlates: 1) intervening pac sequences within the 150 kb genome are ignored during capsid filling; 2) if there is not a pac site available at the 150 kb "milestone" the DNA will not be cut and the capsid will not close.

The fundamental difference between the pac-minus helper virus system of Fraefel et al. and the present pac-plus, oversize helper virus system, is that in the former, the pac sequences are absent and the helper virus genome never enters the capsid. In the latter, the pac sequences are present and the helper virus genome enters the capsid, but the capsid cannot close to generate infectious virus.

There are several advantages to this new approach: 1) deletions in the pac sequence compromise the function of two virus genes, encoding ICP0 and gamma 34.5, which are critical to generating high titers of amplicon vector stocks. In this oversize f-plasmid system embodiment, it is possible to leave these virus functions intact; 2) only one copy of the pac sequence in the f-plasmid is included, and it is placed within sequences different from those in the normal virus genome (i.e., out of normal sequence context), thus, reducing the chance that recombination events can generate an infectious, packageable virus; further, it is placed so that it can be removed to create a pac-minus intermediate using unique restriction enzymes which don't cut in the HSV-1 genome, like PacI or PmeI, or by using site-specific recombinases, such as P1 bacteriophage CRE, yeast FLP (from *Saccharomyces cerevisiae*), yeast R recombinase (from *Zygosaccharomyces rouxii*), etc. (Sauer, B., *Curr. Opin. Biotechnol.* 5:521–527 (1994); Rossant, J., et al., *Nature Med.* 1:592–594 (June 1995); Roder, J., et al., *Nature Genet.* 12: 6–8 (January 1996); Kilby, N.J., et al., *Trends Genet.* 9:413–421 (December 1993)); 3) the advantage of the pac-minus intermediate is that one can efficiently introduce mutations or modifications into the helper virus genome by homologous recombination of targeted HSV-1 sequences containing the pac sequence in permissive mammalian cells (pac-rescue technique, defined above). For example, by introducing a deletion/insertion of pac sequences into the HSV-1 locus encoding the essential viral gene ICP27, one can readily make the oversize pac-minus f plasmid, a pac-plus ICP27-minus helper virus, further reducing the chance of generating replication competent, recombinant helper virus. Alternatively, one can make modifications by homologous recombination in bacteria (Messerle, M., et al., *Proc. Natl. Acad. Sci. USA* 94:14759–14763 (1997); Yang, X W, el al., *Nature Biotechnol.* 15:859–865 (September 1997); Zhang, Y., et al., *Nature Genetics* 20:123–128 (October 1998)).

In addition to the packaging vector, the other component of this packaging system is the herpesvirus amplicon vector. The amplicon vector contains, in a standard plasmid or a large capacity cloning vector (i.e., BAC, YAC), a herpesvirus cleavage/packaging site containing sequence (pac) and an origin of DNA replication (ori) that is recognized by the packaging vector's replication proteins and enzymes. The origin of DNA replication used is preferably a herpesvirus origin of DNA replication. This vector also contains one or more transgene cassette(s), with any heterologous nucleotide sequence(s) of interest. Preferably, the amplicon vector contains: (a) a promoter sequence operably linked to at least one heterologous DNA sequence; and (b) at least one sequence sufficient to permit transcription and processing of mRNA, the translation of which results in an expressed protein. Preferably, the processing sequence is a polyadenylation sequence.

The heterologous sequence can encode any desired protein, such as a therapeutic protein. These sequences can also be designed to achieve gene correction by homologous recombination into endogenous genes in the mammalian genome. The heterologous sequence can also encode antisense DNA, antisense RNA, a ribozyme, or a desired immunogen, such as an antigenic protein. It can also encode specific peptide sequences that will generate an immunogenic reaction.

It is to be understood that both the foregoing general description and the following detailed description are exemplary and explanatory and are intended to provide further explanation of the invention as claimed.

BRIEF DESCRIPTION OF THE FIGURES

In FIG. 1A, the HSV-1 genome (~152 kb) is composed of unique long ($U_L$) and unique short ($U_S$) segments (horizontal lines), which are flanked by inverted repeats (open rectangles): $IR_S$, internal repeat of the short segment; $TR_S$, terminal repeat of the short segment; $IR_L$, internal repeat of the long segment; $TR_L$, terminal repeat of the long segment. The origins of DNA replication, $ori_S$ (●) and $ori_L$ (○), and the DNA cleavage/packaging signals, pac (■), are shown.

In FIG. 1B, cosmid set C6Δa48Δa represents the HSV-1 genome deleted for the pac signals (X) and includes cos6Δa, cos14, cos28, cos48Δa, and cos56.

FIG. 1C shows transfer plasmid fH98-102pac, which is based on the single-copy F-plasmid from *E. coli*. The transfer plasmid contains: (i) sequences between nucleotides 98,968 and 102,732 of the HSV-1 genome to facilitate homologous recombination with HSV-1 DNA from cosmid set C6Δa48Δa, and (ii) the HSV-1 pac signal flanked by recognition sites for restriction endonuclease PacI.

FIG. 1D shows a hypothetical structure of replication competent virus (rHSVf) generated in 2-2 cells upon co-transfection of transfer plasmid fH198-102pac and the five clones of cosmid set C6Δa48Δa. DNA isolated from rHSVf was digested with PacI, a fragment of ~60 kb was isolated, self-ligated, and then electroporated into *E. coli* DH10B.

FIG. 1E shows the predicted structure of a bacterial artificial chromosome (BAC) carrying the HSV-1 genome deleted for the pac signals (fHSVΔpac). The sites for restriction endonucleases, KpnI (K), DraI (D), HindIII (H), BglII (B), and the resulting fragment sizes are indicated. Numbers in bold represent fragment sizes that differ from the original HSV-1 fragments because of the deletion in the pac signals or the insertion of the transfer plasmid.

FIGS. 3A and 3C, 5× magnification; FIGS. 3B and 3D, 20× magnification.

FIG. 5 depicts schematically the packaging of HSV-1 amplicons using fHSVΔpacΔ27 as helper virus.

In FIG. 8A, Mice were injected i.d. with 50 μg fHSVΔpac DNA (○), 50 μg psOVA control DNA (X), or $10^6$ t.u. of HSV-1 amplicon vector pHSVGFP (Δ) and, two weeks later, boosted with the same amount of DNA or vector. Ten days after the booster immunizations, splenocytes were isolated, restimulated in vitro, and analyzed for HSV-1-specific CTL activity in a 4-hour $^{51}$Cr release assay. Results are expressed as the specific lysis at various effector to target (E:T) ratios.

In FIG. 8B, two groups of three mice were immunized once with 1.5 μg of fHSVΔpac DNA by gold-particle bombardment (○, □), and a third group of three mice was injected with $10^9$ PFU of DISC HSV-1 (●). Two weeks later, splenocytes from the three mice in each group were isolated, restimulated separately, and tested individually for CTL activity as described in FIG. 8A. The mean (+/− SD) of three assays is shown.

In FIG. 8C, three groups of three mice were immunized with 1.5 μg fHSVΔpac DNA by gold-particle bombardment (○, □), and a fourth group of three mice was immunized with $10^9$ PFU of DISC HSV-1 by injection (●). The animals were boosted 2 weeks later with the same reagents. Ten days after the booster immunization, the draining lymph node cells of the mice of each group were pooled and analyzed in a direct overnight $^{51}$Cr release assay. Lysis of non-peptide loaded target cells is subtracted from the data shown.

In FIG. 11A, mice (8 per group) were immunized once (□) or twice (○) with 1.5 μg FHSV Δpac DNA or once with 1.5 μg psOVA DNA (■) by gold-particle bombardment, or twice with $10^9$ PFU of DISC HSV-1 by infection (●). Ten days after the last immunization, the animals were challenged intracerebrally with 2×10$^5$ PFU of wt HSV-1 strain F (200 LD$_{50}$).

In FIG. 11B, animals (8 per group) were intravenously inoculated with 100 μl of pooled sera from fHSVΔpacDNA (Δ)- or DISC HSV-1 (▲)-immunized mice. Four hours later, the animals were challenged with wt HSV-1 as described in FIG. 11A.

DETAILED DESCRIPTION OF THE PREFERRED EMBODIMENTS

Figure 1A:
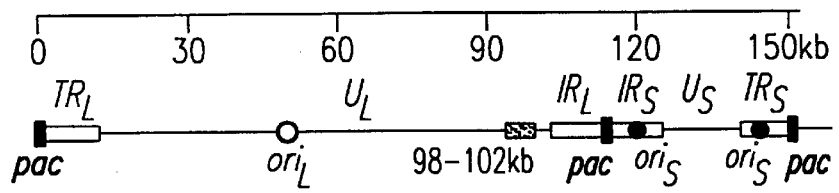
FIGS. 1A–1E depict cloning of the HSV-1 genome as a bacterial artificial chromosome (BAC) in *E. coli*.

The present invention is directed to an improved and simplified herpesvirus amplicon packaging system and method for generating recombinant herpes virus vectors, that are applicable to all herpesviruses. There are over 100 species of herpesvirus. Preferably, the herpesvirus is an alpha herpesvirus such as herpes simplex virus (e.g., HSV-1 or HSV-2), Varicella-Zoster virus, or pseudorabies virus. HSV-1 is a particularly preferred alpha herpesvirus. Other preferred herpesviruses are the Epstein-Barr virus (EBV) and cytomegalovirus CMV).

In an exemplified embodiment, the complete 152 kb HSV-1 genome was cloned, both with and without a pac signal, and stably maintained as a single-copy, F-plasmid based bacterial artificial chromosome (BAC) in *E. coli*. When cloned with a pac signal in BAC (i.e., pac+), the pac signal may be either outside the HSV-1 genome per se, or in the HSV-1 genome within the BAC. Having the pac sequence outside the HSV-1 genome is particularly preferred. Thus, contrary to the method of Fraefel et al., *J. Virol.* 70:7190–7197 (1996), supra, (which utilized a set of 5 overlapping HSV-1 cosmid clones to encode the complete HSV-1 genome, and from which the packaging or pac elements were deleted), the entire packaging defective HSV-1 genome was cloned as a single plasmid DNA by using a BAC cloning vector. This system can then be used to package a wide range of desired nucleotide segments, preferably a DNA segment, into an empty herpesvirus particle (i.e., an HSV amplicon vector) taking advantage of the large transgene capacity of herpesviruses. Recombinant HSV-1 vectors can also be generated by recombination of BAC in bacteria or in mammalian cells using pac-rescue techniques. This technique involves targeted recombination of modified HSV-1 sequences bearing the pac sequence into a pac minus HSV BAC construct, with "rescue" of the pac plus modified genome by transfection and propagation in permissive mammalian cells. By "permissive mammalian cells" is intended mammalian cells which support viral production, such as, e.g., VERO, baby hamster kidney (BHK), and 293 cells, to name a few.

Accordingly, the present invention overcomes the disadvantages of the prior art by providing a system for packaging a herpesvirus amplicon vector by using as a helper virus a packaging vector comprising a single clone, and in particular a bacterial artificial chromosome (BAC), containing the entire HSV-1 genome, said single clone being replication proficient but packaging defective. Thus, in a preferred embodiment, the herpesvirus amplicon can be packaged into infectious particles by cotransfection with a single HSV-BAC packaging vector in permissive mammalian cells, with the resulting amplicon stocks being free of helper virus contamination, yet high in vector titer. The packaging vector provides helper virus functions, such as replicative and virion assembly functions.

The present method for packaging a herpesvirus particle is based upon using a single packaging vector, such as a BAC, which upon delivery into a cell capable of supporting herpesvirus replication will form a DNA segment (or segments) capable of expressing sufficient structural herpesvirus proteins for assembly of herpesvirus particles.

As used herein, the term "BAC (Bacterial Artificial Chromosome)" is intended to mean a cloning and sequencing vector derived from a bacterial chromosome into which a fragment of 100,000 bases or more of DNA can be inserted. BACs are based on the single-copy F-plasmid of *E. coli* and have been demonstrated previously to stably maintain human genomic DNA of >300 kb, and genomes of large DNA viruses, including those of baculovirus and murine cytomegalovirus (Shizuya, H., et al., *Proc. Natl. Acad Sci. USA* 89:8794–8797 (1992); Luckow, V. A., et al., *J. Virol.* 67:4566–4579 (1993); Messerle, M., et al., *Proc. Natl. Acad. Sci. USA* 94:14759–14763 (1997)).

Although a BAC is a particularly preferred large capacity cloning vector, other large capacity cloning vectors known to those skilled in the art can also be used in the present invention. These include, e.g., cosmids (Evans et al., *Gene* 79:9–20 (1989)), yeast artificial chromosomes (YACS) (Sambrook, J., et al., *Molecular Cloning: A Laboratory Manual*, 2$^{nd}$ Edition, Cold Spring Harbor Press, Cold Spring Harbor, N.Y. (1989), PAC P1 phage-based vectors (Ioannou, P. A., et al., *Nature Genetics* 6:84–89 (1994), or virus-based vectors, such as, e.g., CMV, EBV, or baculovirus.

The BAC vector can be constructed using techniques familiar to the skilled artisan. DNA segments representing the entire genome of a herpesvirus can be cloned as a single BAC in *E. coli*. FIG. 1 illustrates the strategy used to clone the HSV-1 genome as a BAC in *E. coli*. See, also Example 1.

The BAC may also be constructed to contain elements of amplicons, e.g., ori, and pac, in order to generate amplicon vectors with a higher transgene capacity (up to 155 kb).

In one embodiment of the above method, the packaging vector (i. e., BAC) is made packaging defective by deleting the herpesvirus cleavage-packaging site containing sequence (pac) sequence entirely or by deleting a sufficient portion to render it incapable of packaging. Alternatively, another strategy is to insert nucleotides into such a site to render it non-functional.

The pac sequence can be deleted from the packaging vector by any of a variety of techniques, such as those described in the present method or those that are well known to those skilled in the art. Preferably, the pac sequence is deleted by digesting with the restriction enzyme PacI, which flanks the pac signal in the BAC. The pac sequence can also be deleted by using techniques such as the recA-assisted restriction endonuclease cleavage technique (RARE: Ferrin, L. J. and Cambering-Adair, R. D., *Science* 254:1494–1497 (1991), which is incorporated herein by reference). Generally, one would use two oligonucleotides to form a region of triple stranded DNA at each of two restriction endonuclease sites. The triple stranded DNA is resistant to methylation by methylase. This third strand can subsequently be removed after a methylation reaction. Double stranded DNA is then digested with the appropriate endonuclease which can cleave the DNA only at the sites previously protected from methylation. Pac sequences can also be removed by homologous recombination in bacteria or site-specific recombination using P1 bacteriophage CRE, yeast FLP, R recombinase, etc. Accordingly, by appropriate design, this method can be used to remove the pac sequence from any desired site. Accordingly, the herpesvirus DNA vectors can express the desired herpesvirus proteins, but because the cleavage/packaging site has been removed, the resultant herpesvirus DNA segment will not have packaging sequences that will cause that DNA to be packaged into the herpesvirus particles, and the virus will not be able to replicate and infect other cells.

The core of the herpesvirus particle is formed from a variety of structural genes that create the capsid matrix. It is necessary to have those genes necessary for matrix formation present in a susceptible cell used to prepare particles. In addition, the necessary envelope proteins which surround the capsid also need to be expressed. Some of these envelope proteins present on the surface of a herpesvirus particle are necessary for viral entry to all cell; others facilitate entry into certain cell types. Thus, the inclusion or exclusion of the functional genes encoding these proteins will depend upon the particular use of the particle. Host range can also be changed by introduction of novel ligands into the envelope (Spear, M. A., et al.,*J. Neurovirol.* 4: 133–147 (April 1998).

In yet another embodiment of the present invention, the packaging vector is made packaging defective by interfering with the capsids ability to close in order to generate infectious virus. That is, the packaging vector contains a pac sequence, however, the sequence is on a DNA fragment that, due to its size, is unable to be packaged into viable HSV particles. For example, when the DNA fragment is too large, the helper virus HSV-1 genome in the packaging vector enters the capsid, but the capsid cannot close to generate infectious virus.

In order to understand this embodiment, it is important to understand the way the virus genome is packaged. By the term "packaged," is intended the incorporation of DNA into the viral capsid and the formation of infectious virions. The virus genome is replicated as a concatenate; it attaches to the open site on the incomplete virus capsid via a terminal pac sequence. The virus DNA is then threaded into the capsid until it is full, with a capacity of about 150 kb. At this point in the normal virus sequence there is another pac site and the DNA is cleaved at this point with subsequent closure of the virus capsid. This process has two important correlates: 1) intervening pac sequences within the 150 kb genome are ignored during capsid filling; 2) if there is not a pac site available at the 150 kb "milestone" the DNA will not be cut and the capsid will not close.

The fundamental difference between the pac-minus helper virus system of Fraefel et al., supra, and the present embodiment which uses a pac-plus, oversize helper virus system, is that in the former, the pac sequences are absent and the helper virus genome never enters the capsid. In the latter, the pac sequences are present and the helper virus genome enters the capsid, but the capsid cannot close to generate infectious virus.

There are several advantages to this new approach: 1) deletions in the pac sequence compromise the function of two virus genes, encoding ICP0 and gamma 34.5, which are critical to generating high titers of amplicon vector stocks. In this oversize f-plasmid system embodiment, it is possible to leave these virus functions intact, thus resulting in increased vector titers; 2) only one copy of the pac sequence in the f-plasmid is included, and it is placed within sequences different from those in the normal virus genome (i. e., out of normal sequence context), thus reducing the chance that recombination events can generate an infectious, packageable virus; further, it is placed so that it can be removed to create a pac-minus intermediate using unique restriction enzymes which don't cut in the HSV-1 genome, like PacI or PmeI, or by using site-specific recombinases, such as, e.g., P1 bacteriophage CRE, yeast FLP (from *Saccharomyces cerevisiae*), yeast R recombinase (from *Zygosaccharomyces rouxii*), etc. (Sauer, B., *Curr. Opin. Biotechnol.* 5:521–527 (1994); Rossant, J., et al., *Nature Med.* 1: 592–594 (June 1995); Roder, J., et al.,*Nature Genet.* 12: 6–8 (January 1996); Kilby, N. J., et al., *Trends Genet.* 9:413–421 (December 1993)); 3) the advantage of the pac-minus intermediate is that one can efficiently introduce mutations or modifications into the helper virus genome by homologous recombination of targeted HSV-1 sequences containing the pac sequence in permissive mammalian cells (pac rescue method, discussed above). For example, by introducing a deletion/insertion of pac sequences into the HSV-1 locus encoding the essential viral gene ICP27, one can readily make the oversize pac-plus helper virus ICP27-minus, further reducing the chance of generating replication competent, recombinant helper virus. Alternatively, one can make modifications by homologous recombination in bacteria (Messerle, M., et al., *Proc. Natl. Acad. Sci. USA* 94:14759–14763 (1997); Yang, X W, et al., *Nature Biotechnol.* 15:859–865 (September 1997); Zhang, Y., et al., *Nature Genetics* 20:123–128 (October 1998)); and 4) pac-plus HSV-1 f-plasmids can also be engineered to remove essentially all HSV-1 sequences except $ori_S$ and to incorporate transgenes up to a theoretical 150 kb capacity and be used as amplicon vectors. In one example of this embodiment, a BAC, containing the HSV-1 genome (the single clone being replication proficient, but packaging defective), was used as a DNA-based vaccine to induce protective immunity against HSV-1. This approach represents a novel generation of DNA-based vaccination strategies for many viral and non-viral antigens. That is, in addition to the HSV-1 genome, any viral, bacterial, or parasitic gene or genome can be cloned into the packaging vector (i.e., fHSVΔpac) to vaccinate against those pathogens. The HSV-1 sequences will then both serve as adjuvants and mediate replication of the vaccine DNA within the host cell nucleus, which increases the amount of antigen presented to the immune system.

The other component of this packaging system is the herpesvirus amplicon vector. The amplicon vector contains a herpesvirus cleavage/packaging site containing sequence (pac) and an origin of DNA replication (ori) which is recognized by the packaging vector's replication proteins and enzymes. The origin of DNA replication used is preferably a herpesvirus origin of DNA replication. This vector also contains a transgene cassette with any heterologous nucleotide sequence of interest. Preferably, the amplicon vector contains: (a) a promoter sequence operably linked to at least one heterologous DNA sequence; and (b) at least one sequence sufficient to permit transcription and processing of mRNA, the translation of which results in an expressed protein. Preferably, the processing sequence is a polyadenylation sequence.

The heterologous sequence can encode any desired protein, such as a therapeutic protein. These sequences can also be designed to achieve gene correction by homologous recombination into endogenous genes in the mammalian genome. The heterologous sequence can also encode antisense DNA, antisense RNA, a ribozyme, or a desired immunogen, such as an antigenic protein. It can encode specific peptide sequences that will generate an immunogenic reaction.

The heterologous nucleotide sequence can encode a therapeutic protein, such as, for example, one that compensates for an inherited or acquired deficiency. Examples of therapeutic proteins include neurotransmitter biosynthetic enzymes, e.g., tyrosine hydroxylase for the treatment of Parkinson's disease; neurotrophic factors including neurotrophins, e.g., nerve growth factor for the treatment of Alzheimer's disease, one can also use nerve growth factor receptor and the trk receptor; hypoxanthine-guanine phosphoribosyl transferase (HGPRT) for the treatment of Lesch Nyhan disease; β-hexosaminidase α chain for the treatment of Tay Sachs disease; insulin for the treatment of diabetes. Receptors can also be prepared, e.g. the nerve growth factor receptor, the trk receptor, etc. Because the insert can be large, it is possible to encode a series of different proteins with large promoter elements. For example, one can encode a series of proteins that form a receptor-ligand complex under cell-specific or exogenously regulated gene expression.

Other proteins include, for example,.signal transduction enzymes, e.g., protein kinase c; transcription factors, e.g., c-fos, NF-Kβ; oncogenes, e.g., erbB, erbB-2/neu, ras; neurotransmitter receptors, e.g., glutamate receptor, dopamine receptor; heat shock proteins; anti-apoptotic factors; anti-oncogenic proteins; prodrug activating enzymes; immune enhancers; imaging proteins; and angiogenic or anti-angiogenic factors. In addition, normal genes can be carried for gene correction or supplementation of normal gene products.

The heterologous nucleotide sequence can also encode antisense molecules (DNA or RNA) or ribozymes. These molecules can be used to regulate gene expression associated with a particular disease. The antisense molecules are obtained from a nucleotide sequence by reversing the orientation of the coding region with regard to the promoter. Thus, the antisense RNA is complimentary to the corresponding mRNA. For a review of antisense science, see, Green et al., *Ann. Rev. Biochem.* 55:569–597 (1986), which is herein incorporated by reference. The antisense sequence can contain modified sugar phosphate backbones to increase stability and make them less sensitive to RNA sensitivity. Examples of the modifications are described in Rossi et al., *Pharmacol. Ther.* 50(2):245–354 (1991). Ribozymes can also be used to degrade mutant or overexpressed mRNA (Cech, T. R., et al., *Ann. Rev. Biochem.* 59:543–568 (1990)).

The heterologous nucleotide sequence can also encode specific antigenic peptide sequences that will generate an immunogenic reaction.

The heterologous nucleotide sequence is preferably operably linked to a promoter sequence capable of directing transcription of the sequence in a desired target cell. The promoter can be, for example, the HSV-1 IE and IE 4/5 promoters. Promoters capable of directing transcription of the heterologous sequence in a specific target cell can also be used. For example, if the target cell is a neuronal cell, a promoter such as the neuron specific enolase promoter (Forss-Petter et al., *Journal of Neuroscience Research* 16:141–156 (1986)) can be used. The rat tyrosine hydroxylase (TH) promoter can support cell type specific expression in the midbrain (Song, S., et al., *J. Neurochem.* 68:1792–1803 (May 1997)). Furthermore, the use of inducible promoters or other inducible regulatory sequences, which are well known in the art, in some embodiments are preferred. For example, one could use a TAR sequence operably linked to a gene encoding a desired protein if one is targeting an HIV infected cell. In such a system, the tat protein produced by such an infected cell will trans activate the expression of the gene operably linked. One can also use drug-regulated promoters, such as ecdysone, tetracycline and dimerizing systems, as well as locus control regions, matrix attachment sites, and transcription stop sequences to prevent override.

The potential contamination of vector stocks with replication-competent, although attenuated, helper virus ($10^{-6}$~$10^{-4}$) could hamper the use of amplicon vectors for practical gene therapy applications. Therefore, in order to minimize the possibility of a recombination event between the amplicon vector and the packaging vector, generating a replication-competent wild-type herpesvirus, it is desirable that the packaging vector has a minimal degree of homology with the amplicon vector and/or that the packaging vector does not have at least one functional herpesvirus gene encoding an essential protein for virus replication. Thus, preferably one would reduce the sequence overlap between the packaging vector and the amplicon vector so that there are no regions of twenty nucleotides or more showing more than forty percent sequence homology with the herpesvirus DNA segment with the exception of the origin of DNA replication (ori) used, pac, and any herpesvirus promoters used. Still more preferably, one could use different promoters in these two different vectors. Even more preferably, one would use different origins of DNA replication. These goals can be accomplished by a variety of means known in the art based upon the present disclosure.

For example, if one is using as the herpesvirus, HSV-1, and uses the $ori_S$ in the packaging vector, one would delete or substitute a different ori for $ori_S$ in the herpesvirus DNA vector segment. As an alternative to substituting the ori in the herpesvirus vector, one might substitute the ori in the packaging vector. More preferably, one could replace the HSV-1 ori with an ori from a different member of the herpesvirus family. For example, the bovine herpesvirus ori is conserved in the core ori region and then diverges and could be used. Similarly, the promoters in the herpesvirus DNA segment could be replaced with other herpesvirus promoters so that they are different than the promoters in the packaging vector. For example, with the HSV-1 ori$_S$, the IE 3 and IE 4/5 promoters are intermingled in the segment before the ori. These promoters could be replaced with other HSV-1 IE promoters such as IE 1 and IE 2. Alternatively, but less preferred is substituting the promoters in the herpesvirus DNA segment. When this is done, care must be taken to use a promoter that will provide the appropriate timing for expression of a particular gene. There are additional alternatives for reducing homology between the packaging vector and the herpesvirus vectors such as using a smaller ori$_S$ fragment in the vector. However, the shorter ori fragment can reduce the titer yield. One could use any one of these approaches or a combination thereof to reduce the level of homology.

Alternatively or in combination with the above approach of reducing homology, one can alter the sequence of a gene from the herpesvirus DNA segment so that it does not encode a functional protein. As used herein, "functional" means a protein having wild-type activity. For example, one could delete an essential gene or a sufficient portion thereof or a gene necessary for viral DNA replication or cytotoxicity. In addition, one could insert nucleotides altering the reading frame or otherwise preventing expression of a functional protein. For example, with HSV-1, the IE 2 (ICP27) and IE 3 (ICP4) genes are preferred candidates for inactivating an essential gene. This is in part because cell lines that express these genes are known in the art and can be used to obtain expression of the particle without the risk of generating a wild-type virus. For example, E5 cells express IE 3 and 2-2 cells express IE 2. Accordingly, one can routinely express the necessary herpesvirus proteins in desired cell lines.

In Example 2, the inventors tested whether the disruption of an essential gene and/or an increase in the size of the HSV-1 BAC clone (in addition to the existing safety feature of inactivated packaging signals in the HSV-helper genome) would reduce further the risk of contamination with replication-competent helper viruses. Therefore, in Example 2, the ICP27 coding sequence was deleted from fHSVΔpac through homologous recombination in E. coli. In addition, the size of the clone was increased to 170 kb. The resulting clone, fHSVΔpacΔ27, supported the replication and packaging of co-transfected amplicon DNA only when ICP27 was provided in trans. The resulting vector stocks had titers of >$10^7$ t.u./ml and were free of detectable, replication-competent helper viruses (<$10^{-8}$).

Depending upon the particular use for these herpesvirus vectors, one can use well-known techniques to alter the herpesvirus DNA segment to inactivate genes that encode proteins present in the particle which cause cytopathic effects. For example, inactivating those proteins that affect cellular protein synthesis. In HSV-1, the UL 41 gene products (which are 57 kb and 58 kb) direct both an inhibition of cellular protein synthesis and the degradation of cellular mRNA (Read, G. S., et al., J. Virol. 67:7149–7160 (1993)).

UL 13 encodes a protein kinase which can direct a shut off of cellular protein synthesis. This protein kinase both autophosphorylates and phosphorylates several HSV-1 proteins (Cunningham, C., et al., J. Gen. Virol. 73:303–311 (1992); Coulter, L. J., et al., J. Gen. Virol. 74:387–395 (1993)). Deletion of UL 13 significantly reduces the shut off of cellular protein synthesis indicating that the gene product acts in cooperation with the UL 41 gene product. However, it does not phosphorylate the UL 41 gene product.

One can alter genes that can affect cellular gene expression. For example, with HSV-1, VP 16 increases the activity of IE promoters and may also potentially effect expression of cellular genes. The UL 48 gene encodes the transactivator. However, the UL 48 gene product itself is essential for HSV-1 particle assembly and this portion of the protein cannot be destroyed but the protein can be altered to destroy or reduce its transactivation activity. (See, Ace, C. I., et al., J. Gen. Virol. 69:2595–2605 (1988); Ace, C. I., et al., J. Virol. 63:2260–2269 (1989)).

The UL 46 gene product increases the transcriptional activity of the UL 48 gene product and the UL 47 gene product decreases the transcriptional activity of the UL 48 gene product. These gene products form a complex with DNA and the UL 48 gene product and a cellular factor (McKnight et al., Journal of Virology 61:992–1001 (1987); Carpenter, D. E., et al., J. Gen. Virol. 72:3077–3084 (1991)).

The US 11 gene product associates with a 60 S ribosomal RNA in the nucleolus and inhibits processing of a specific HSV-1 encoded RNA and binds to 60 S ribosomal subunits in the cytoplasm (Roller, R. J., et al., J. Virol. 68:2830–2839 (May 1994))

There are genes which encode proteins that can affect phosphorylation of cellular proteins. For example, HSV-1 encodes two ser/thr protein kinases; the aforementioned UL 13 and also US 3. Protein phosphorylation can trigger immune reactions and neural cells use signal transduction pathways to process information. Both immune responses and information processing can produce effects that persist long after the HSV-1 particle proteins are degraded. One would preferably minimize these effects by inactivating these proteins using standard techniques based upon the present disclosure. Inactivation can be by mutations to delete the gene encoding the protein, additions or substitutions to inactivate the proteins.

One can also reduce immune responses to vectors by inactivating genes encoding non-essential HSV-1 glycoproteins that are present on the surface of the particle. While in some instances it is desirable to mimic the herpes particle as much as possible, in other instances there are many proteins present on the surface of the particle that are not necessary and will only help to generate an immune response. The herpesvirus particles contain many glycoproteins. For example, the HSV-1 particle contains about 12 HSV-1 encoded glycoproteins. Two of these glycoproteins are essential to the HSV-1 lytic cycle: UL 27 and US 6 encode gB and gD which mediate the initial events in infection (e.g., membrane-membrane fusion between the HSV-1 particle and the plasma membrane of the cell). UL 10 encodes gM and deletion mutants in UL 10 grow well in culture fibroblast cells (MacLean, C. A., et al., J. Gen. Virol. 72:897–906 (1991); Baines, J. D., et al., J. Virol. 65:938–944 (1991); MacLean, C. A., et al., J. Gen. Virol. 74:975–983 (1993)). UL 43 encodes a membrane associated protein of unknown function but a deletion mutant grows well in cultured fibroblast cells (MacLean, C. A., et al., J. Gen. Virol. 72:897–906(1991)). UL44 encodes gC and a mutation grows well in cultured fibroblast cells (Hidaka, Y., et al., Arch. Virol. 113:195–207 (1990)). US 4 encodes gG and a lacZ insertion mutant, which disrupts expression of US 4, and grows well in cultured fibroblast cells (Balan, P., et al., J. Gen. Virol. 1994)). US 5 encodes gJ and a LacZ insertion mutant, which disrupts expression, and grows well in cultured fibroblast cells. Id. US 7 and US 8 encode gI and gE respectively. These two glycoproteins form a complex which function as a receptor for the Fc region in immunoglobulin class G (IgG) and thus partially protect both the HSV-1 particle and infected cells from immune system effector mechanisms (Frank, I., et al., *Journal of Virology* 63:4479–4488 (1989)). Mutants which disrupt expression of either of these proteins grow well in cultured fibroblast cells. UL 56 encodes a protein contained in the HSV-1 particle which is recognized by IgM and IgG antibodies against HSV-1. Deletion mutants grow well in cultured fibroblast cells and show reduced pathogenicity upon injection into mice (Rosen-Wolff, A., et al., *Virus Research* 20:205–221 (1991)). One can inactivate any number of these genes depending upon the manner in which the particle is to be used.

A cell susceptible to infection and DNA replication by a herpesvirus is transfected by the vectors to prepare the viral particle in a helper-virus free system. One can prepare the vectors in culture. One would then harvest the particles, purify them, and inject them by means well known in the art. More preferably, one would purify the particles, and then use those to transfect the desired cells.

One can prepare transient or stable cell lines that express the herpesvirus DNA segment by standard techniques based upon the present teaching. For example, all toxic genes can be deleted or downregulated and the remaining HSV-1 genome maintained as an episome. Such stable herpesvirus DNA cell lines are a preferred source for transfection by the amplicon vector. Alternatively, cells can be cotransfected or coinfected by both the amplicon vector and the packaging vector. One can coinfect cells with the packaging vector as it isn't packaged in HSV-1 virions; one can package it in another type of virion, e.g., EBV.

The herpesvirus particle of the present invention can be used to deliver heterologous DNA to a target cell. The target cell may be in vivo, ex vivo, or in culture. Mammalian target cells are preferred. The target cell can be a dividing or quiescent cell. Quiescent cells include postmitotic cells. The preferred postmitotic cells are glia, neurons, hepatocytes, muscle cells, macrophages, etc.

Introduction of the viral particle carrying the heterologous gene to be delivered to the target cell may be effected by any method known to those of skill in the art. For example, stereotaxic injection can be used to direct the viral particles to desired locations in the brain. Stereotaxic surgery is performed using standard neurosurgical procedures (Pellegrino, L. J. and Cushman, A. J., "Methods in Psychobiology," Academic Press, New York, N.Y., pp. 67–90 (1971)). Additionally, the particles can be delivered by intracerebroventricular ("icv") infusion using a minipump infusion system, such as a SynchroMed Infusion System. A recent method based on bulk flow, termed convection, has also proven effective at delivering large molecules to extended areas of the brain and may be useful in delivering the viral particle to the target cell (Bobo, R. H., et al., *Proc. Natl. Acad. Sci.* 91:2076–2080 (1994); Morrison, P. F., et al., *Am. J. Physiol.* 266:292–305 (1994)). Other methods can be used including catheters, intravenous, parenteral, intraperitoneal and subcutaneous injection, oral or other known routes of administration.

One would inject a sufficient amount of the viral particles to obtain a serum concentration in the tissue containing the target cell of the therapeutic protein ranging between about 1 µg/ml to 20 µg/ml. More preferably between about 0.1 µg/ml to 10 µg/ml. Still more preferably, between about 0.5 µg/ml to 10 µg/ml.

For example, solid dose forms that can be used for oral administration include capsules, tablets, pills, powders, liposome emulsions, and granules. In such solid dose forms, the active ingredient, i.e., empty virus particle, is mixed with at least one inert carrier such as sucrose, lactose or starch. Such dose forms can also comprise additional substances other than inert diluents, e.g., lubricating agents, such as magnesium stearate. Furthermore, the dose forms in the case of capsules, tablets and pills may also comprise buffering agents. The tablets, capsules and pills can also contain time-release coatings to release the particles over a predetermined time period.

For parenteral administration, one typically includes sterile aqueous or non-aqueous solutions, suspensions or emulsions in association with a pharmaceutically acceptable parenteral vehicle. Examples of non-aqueous solvents or vehicles are propylene glycol, polyethylene glycol, vegetable oils such as olive oil and corn oil, gelatin and injectable organic esters, such as ethyl oleate. These dose forms may also contain adjuvants such as preserving, wetting, emulsifying and dispersing agents. They may be sterilized by, for example, filtration through a bacterial-retaining filter, by incorporating sterilizing agents into the composition, by irradiating the compositions, etc., so long as care is taken not to inactivate the virus particle. They can also be manufactured in a medium of sterile water or some other sterile injectable medium before use. Further examples of these vehicles include saline, Ringer's solution, dextrose solution and 5%.human serum albumin. Liposomes may also be used as carriers. Additives, such as substances that enhance isotonicity and chemical stability, e.g., buffers and preservatives, may also be used.

The preferred range of active ingredient in such vehicles is in concentrations of about 1 mg/ml to about 10 mg/ml, more preferably, about 3 mg/ml to about 10 mg/ml.

The present invention is further illustrated by the following Examples. These Examples are provided to aid in the understanding of the invention and are not to be construed as a limitation thereof.

EXAMPLE 1

Materials and Methods

Cell Culture

African green monkey kidney cells (VERO76, ECACC) and human embryonic kidney cells (293; ATCC) were propagated in Dulbecco's modified minimal essential medium (DMEM) supplemented with 100 U/ml penicillin and 100 µg/ml streptomycin (P/S), and 10% fetal bovine serum (FBS). 2-2 cells (kindly provided by Dr. R. Sandri-Goldin, University of California, Irvine, Calif.; Smith, I. L., et al., *Virology* 186:74–86 (1992)), which are VERO-derived cells that constitutively express the HSV-1 ICP27 protein, were cultivated in DMEM containing P/S, 10% FBS and 500 µg/ml G418 (Geneticin; GIBCO, BRL).

Construction of HSV-1 Transfer Plasmid fH98-102pac

To construct pBXPBPX, plasmid pBsSK+ (Stratagene) was digested with XhoI and ligated to the synthetic oligonucleotide duplex 5' tcgagggcccttaattaagatcttaattaagggccc 3', (SEQ ID NO:1) as a method to substitute the pBsSK+ XhoI site by the polylinker XhoI-PacI-BglII-PacI-XhoI. Plasmid pHSVPrPUC (kindly provided by Dr. H. Federoff, University of Rochester, N.Y.), Bergold, P. J., et al., *Proc. Natl Acad. Sci. USA* 90:6165–6169 (July 1993), was digested with XhoII, and the 1.4 kb-fragment which contains the HSV-1 DNA cleavage/packaging signal (pac) was inserted into the BglII site of pBXPBPX. The resulting plasmid, pBXPpacPX, was digested with XhoI, and the 1.4 kb-fragment was inserted into the unique XhoI site of pBeloBAC11 (Research Genetics, Inc.) forming pBeloBACpac. A ~4 kb HincII fragment (nucleotides, nt, 98,742–102,732 of the HSV-1 genome; McGeoch, D. J., et al., *J. Gen. Virol.* 69:1531–1574 (1988)) was isolated from cos56 of HSV-1 cosmid set C (kindly provided by Drs. C. Cunningham and A. J. Davison, MRC Virology Unit, Glasgow, UK; Cunningham, C. and Davison, A. J., *Virology* 197:116–124 (1993)) and inserted first into the EcoRV site of pBsSK+. From the resulting subclone, pBH98-102, a ~4-kb BamHI fragment (nt 98,968–102,732 of the HSV-1 genome) was isolated and inserted into the unique BamHI site of pBeloBACpac. The resulting transfer plasmid, fH98-102pac, was used to target integration of (i) the HSV-1 pac signal flanked by PacI restriction sites, and (ii) *E. coli* F-factor-derived sequences into the HSV-1 genome between nt 98,968 and 102,732 (FIG. 1C).

Construction of rHSVf

Figure 1B:
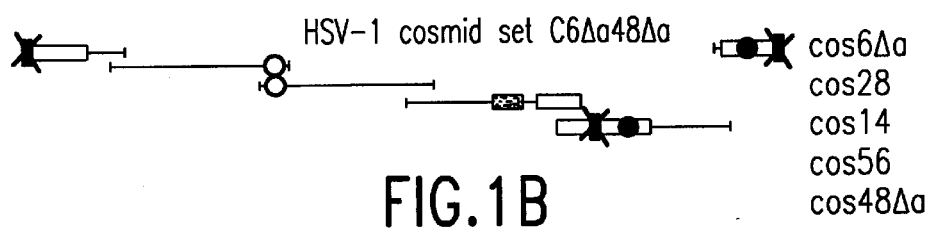
Figure 1C:
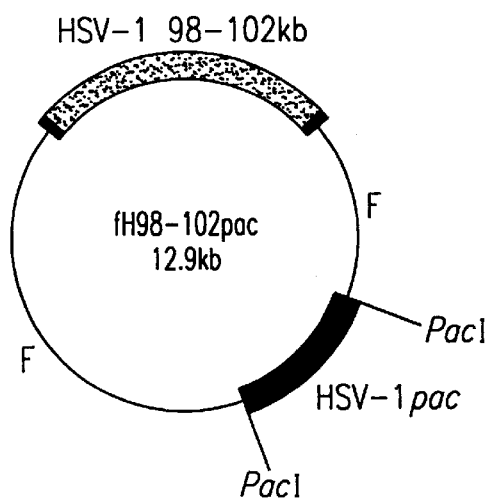

The five cosmids of set C6Δa48Δa (FIG. 1B; Cunningham, C. and Davison, A. J., *Virology* 197:116–124 (1993); Fraefel, C., et al., *J. Virol.* 70:7190–7197 (1996)) were digested with PacI to excise the HSV-1 inserts and purified by phenol extraction. 2-2 cells were plated at a density of 1×10$^6$ cells per 60-mm-diameter tissue culture dish. The following day, the cells were transfected with 0.5 μg of fH98-102pac DNA and 0.4 μg of each cosmid DNA by the LipofectAMINE procedure according to instructions provided by the manufacturer (GIBCO, BRL). Three days after transfection, the cells were scraped into the medium, the suspension was frozen and thawed three times, cell debris was removed by centrifugation (10 minutes; 1,400 g), and titers (PFU/ml) of replication-competent virus (rHSVf, see FIG. 1D) were determined by standard plaque assays on VERO cells.

Construction of fHSVΔpac and fHSVpac+ rHSVf (FIG. 1D) was amplified over 3 passages on VERO cells. When cytopathic effect (CPE) was complete after the third passage, the cells (from 12×T175 tissue culture flasks) were scraped into the medium, the suspension (240 ml) was frozen and thawed three times, and cell debris was removed by centrifugation (10 minutes; 1,400 g). Following centrifugation for 1 hour at 28,000 g and 4° C., the supernatant was discarded, and the virus pellet was resuspended in 80 ml of balanced salt solution (BSS; 137 mM NaHCl, 5.4 mM KCl, 10 mM Tris-HCl, pH 7.6). After centrifugation for 30 minutes at 28,000 g and 4° C., the pellet was resuspended in 5.5 ml TE buffer (10mM Tris-HCl, 10 mM EDTA; pH 7.5) and 150 μl of a 20 mg/ml solution of proteinase K. The suspension was incubated for 1 hour at 37° C., and after the addition of 300 μl of a 10% SDS solution, further incubated overnight at 37° C. Following phenol-chloroform extraction and ethanol precipitation, virus DNA was resuspended in TE buffer, digested completely with PacI restriction endonuclease, and then fractionated by electrophoresis through 0.4% low-melt agarose (GIBCO, BRL) at 40 V overnight.

Figure 1E:
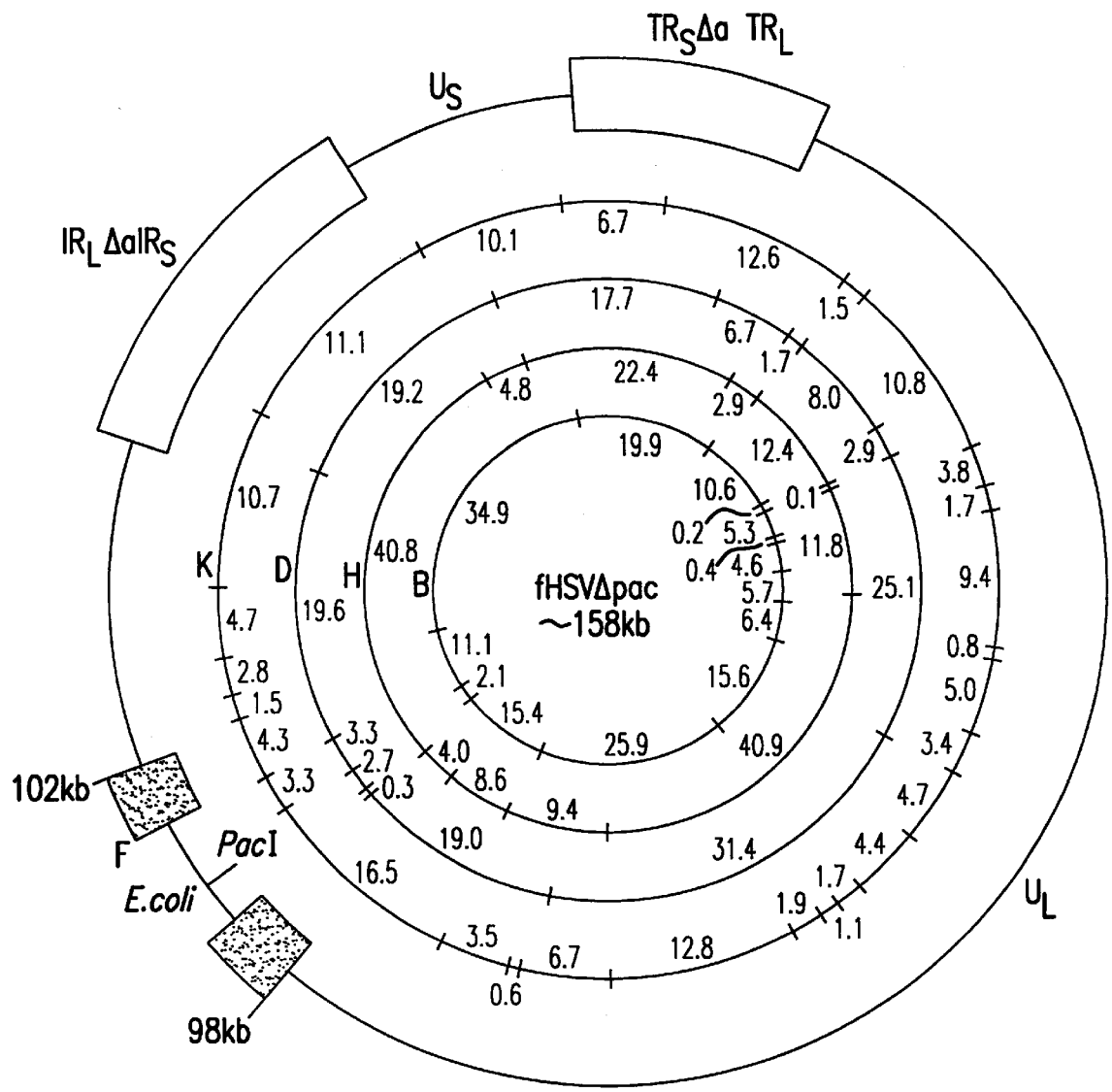
Figure 2:
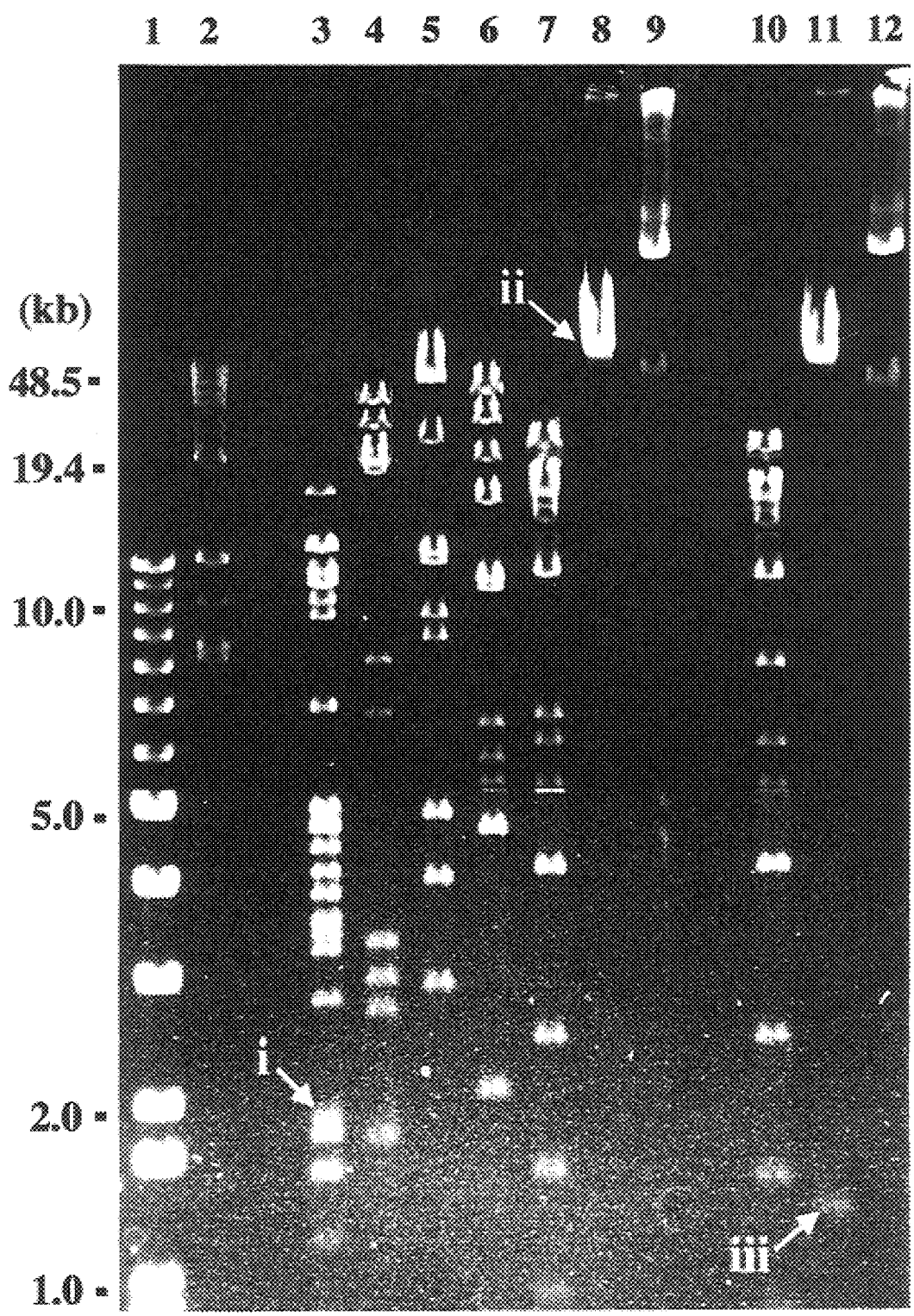
FIG. 2 depicts an analytical agarose gel showing restriction endonuclease patterns of BAC DNA. The reaction mixtures were loaded on a 0.4% agarose gel, and the fragments were separated overnight at 40 V in TAE electrophoresis buffer and stained with ethidium bromide. Lane 1: 1-kb Plus DNA ladder (GIBCO, BRL). Lane 2: high molecular weight DNA standard (GIBCO, BRL). Lanes 3–9: fHSVΔpac DNA digested with KpnI, DraI, HindIII, BglII, EcoRI, PacI, or undigested. The 1.9 kb KpnI fragment containing HSV-1 $ori_L$ (arrow i, lane 3), and the 158 kb PacI fragment (linearized fHSVΔpac; arrow ii, lane 8) are indicated. Lanes 10–12: fHSVpac+ DNA digested with EcoRI, PacI, or undigested. The 1.4 kb PacI fragment containing the HSV-1 pac signal is indicated (arrow iii, lane 11). To provide adequate contrast for the fragments with different sizes in the entire gel, this gel image is composed of three pictures with different exposures.

A band corresponding to ~160 kb was excised from the gel, treated with β-agarase I (New England Biolabs), and the purified DNA was self-ligated with T4 DNA ligase. The ligation products were electroporated into electrocompetent *E. coli* DH10B cells according to instructions provided by the supplier (GIBCO, BRL). Miniprep DNA of several colonies that appeared on LB plates containing 12.5 μg/ml of chloramphenicol (LB$^{CM}$). was prepared by alkaline lysis, and clones that contained the HSV-1 genome with pac signals deleted (fHSVΔpac) were characterized by restriction enzyme analysis (FIGS. 1E and 2). To construct fHSVpac+, tHSVΔpac DNA was digested with PacI, treated with alkaline phosphatase to prevent religation, and then ligated to the 1.4-kb PacI fragment isolated from pBXP-pacPX (see above). After electroporation of the ligation products into *E. coli* DH10B and selection of colonies on LBCM plates, clones which contained the HSV-1 pac signal were characterized by restriction enzyme analysis (FIG. 2).

Generation of Virus Plaques From fHSVpac+

Large amounts of BAC DNA were prepared from 11 cultures grown in LB$^{CM}$. Plasmid DNA was extracted by alkaline lysis and purified first over QIAGEN Tip-500 columns, as described by the manufacturer (Qiagen, Inc.), and then by cesium chloride equilibrium centrifugation (Sambrook, J., et al., "Molecular Cloning," in *A Laboratory Manual*, Cold Spring Harbor Laboratory Press, Cold Spring Harbor, N.Y. (1989)). BAC DNA (fISVΔpac or fHSVpac+) or HSV-1 cosmid DNA (set C or set C6Δa48Δa; Cunningham, C. and Davison, A. J., *Virology* 197:116–124 (1993); Fraefel, C., et al., *J. Virol.* 70:7190–7197 (1996) was transfected into 2-2 cells by using LipofectAMINE as described above, except that following transfection, the cultures were incubated in DMEM that contained 2% FBS and 0.8% carboxymethyl cellulose (BDH Chemicals Ltd., Poole, UK). After 2 days, the cultures were stained with crystal violet to visualize plaques.

Packaging of Amplicon DNA into HSV-1 Virions and Titration of Vector Stocks 2-2 cells were co-transfected with 0.6 μg of pHSVGFP amplicon DNA (expresses the gene for green fluorescent protein, GFP; Aboody-Guterman, K.S., et al., *NeuroReport* 8:3801–3808 (1997)) and 2 μg of fHSVΔpac DNA by the LipofectAMINE procedure, described above. After three days, the cells were scraped into the medium, the suspension was frozen and thawed three times, and cell debris was removed by centrifugation (10 minutes; 1,400 g). To determine vector titers (t.u./ml), 293 cells were infected, and 24 hours later, green fluorescent cells were counted using a fluorescence microscope equipped with a filter set for detection of enhanced GFP. Titers of replication-competent virus (PFU/ml) were determined by standard plaque assays on VERO cells. For gene transfer experiments into the rat brain and liver, pHSVGFP vector stocks were filtered (0.8 μm cellulose nitrate membrane filters; Nalgene, Rochester, N.Y.) and then centrifuged for 2.5 hours at 100,000 g through 25% sucrose (in PBS). The pellet was resuspended in Hank's BSS and the titer of pHSVGFP vector was determined on 293 cells, as described above.

Gene Transfer Into Rat Brain and Rat Liver

Animal studies were performed in accordance with guidelines issued by the Massachusetts General Hospital Subcommittee on Animal Care. Inoculations of HSV-1 amplicon vectors into experimental animals, and care of these animals were carried out in approved BL-2 rooms. Male CD Fisher rats (300 g; Charles River Laboratories) were anesthetized with ketamine (12.5 mg) and xylazine (2.5 mg). Stocks of pHSVGFP vector were either delivered (7.5×10$^5$ t.u. in 10 μl) under stereotaxic guidance into the right hippocampus (AP −3.5, R 2.0, V −3.5; Paxinos, G. and Watson, C., "The Rat Brain in Stereotaxic Coordinates," Academic Press, Sidney, Australia (1986)), or injected (7.5×10$^6$ t.u. in 100 μl) under the perisplanchnic membrane into the caudal liver lobe. After 3 days, the animals were anesthetized and perfused with PBS followed by 4% paraformaldehyde in PBS. Brains and livers were post-fixed overnight in 4% paraformaldehyde in PBS, cryoprotected for 2 days with 30% sucrose in PBS, and cut into 20-μm cryostat sections.

The sections were mounted on glass slides, coverslipped by using Gel/Mount™ medium (Biomeda Corp., Foster City, Calif.), and examined with a confocal laser microscope (Bio-Rad MRC-1024).

Results and Discussion

HSV-1 cosmid sets have been employed to facilitate the construction of recombinant viruses and, after deletion of the HSV-1 pac signals, to mediate the helper virus-free packaging of HSV-1 amplicons into virions (Cunningham, C. and Davison, A. J., *Virology* 197:116–124(1993); Fraefel, C., et al., *J. Virol.* 70:7190–7197 (1996)). Although, the packaging of amplicons requires the cells to be co-transfected by all five clones of the cosmid set and the amplicon DNA, the resulting vector titers are relatively high with $10^6$–$10^7$ t.u./ml.

The goal of this Example was to assess whether a single clone, in particular a bacterial artificial chromosome (BAC) containing the HSV-1 genome deleted for the pac signals, could further increase the titers of amplicon vector stocks. BACs are based on the single-copy F-plasmid of *E. coli* and have been demonstrated previously to stably maintain human genomic DNA of >300 kb, and genomes of large DNA viruses, including those of baculovirus and murine cytomegalovirus (Shizuya, H., et al., *Proc. Natl. Acad. Sci. USA* 89:8794–8797 (1992); Luckow, V. A., et al., *J. Virol.* 67:4566–4579 (1993); Messerle, M., et al., *Proc. Natl. Acad. Sci. USA* 94:14759–14763 (1997)).

Cloning of the HSV-1 Genome as a Bacterial Artificial Chromosome (BAC)

FIG. 1 illustrates the strategy used to clone the HSV-1 genome as a BAC in *E. coli*. First, transfer plasmid fH98-102pac was designed to have the following features: (i) sequences which mediate homologous recombination with HSV-1 DNA between nucleotides 98,968 and 102,732 (McGeoch, D. J., et al., *J. Gen. Virol.* 69:1531–1574 (1988)); (ii) the HSV-1 DNA cleavage/packaging signal (pac) flanked by recognition sites for restriction endonuclease PacI; and (iii) *E. coli* F-factor-derived sequences which allow amplification of the clone as a single-copy plasmid in bacteria (Willets, N. and Skurray, R., "*Escherichia coli* and *Salmonella Typhimurium*," in *Cellular and Molecular Biology* 2:1110–113, F. C. Neidhardt, ed., Am. Soc. Microbiol., Washington, (1987); FIG. 1C)). Transfer plasmid fH98-102pac was co-transfected with five cosmids which represent the entire HSV-1 genome as overlapping clones, but which were previously mutated to remove the pac signals (cosmid set C6Δa48Δa; FIG. 1B; Cunningham, C. and Davison, A. J., *Virology* 197:116–124 (1993); Fraefel, C., et al. *J. Virol.* 70:7190–7197 (1996)). Three days after transfection, progeny virus was harvested and demonstrated to contain replication-competent virus (rHSVf) by standard plaque assay on VERO cells ($1.25 \times 10^4$ PFU/ml). The cosmid clones can form a complete replication-competent virus genome via homologous recombination between the overlapping sequences. However, these virus genomes are only packageable if a pac signal is acquired through integration of the transfer plasmid fH98-102pac via a single cross-over within the ~4 kb of sequence homology (nt 98,968-102,732 of the HSV-1 genome).

Figure 1D:
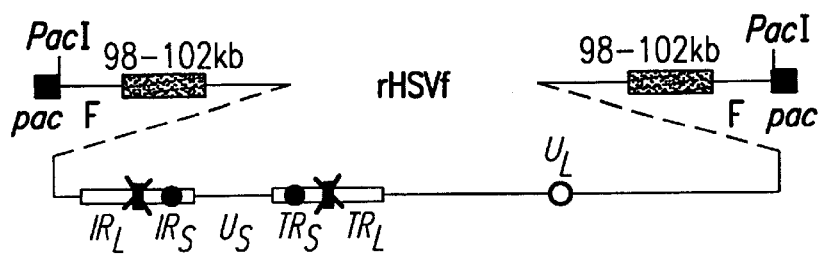

After amplification of this original stock of rHSVf, virion DNA was isolated and digested with PacI (which does not cut wild-type HSV-1 DNA) to remove the pac signal (FIG. 1D). From this digestion, a DNA fragment of approximately 160 kb was isolated and self-ligated with T4 DNA ligase. The ligation product was then electroporated into electro-competent *E. coli* DH10B cells. Of the colonies appearing on selective plates, several clones that contained large inserts were identified, and one clone, designated fHSVΔpac, was further characterized by restriction enzyme analysis. Digestion with different restriction endonucleases, including KpnI, DraI, HindIII, BglII, EcoRI and PacI, identified all bands predicted from the published HSV-1 sequence, including the ~1.9-kb Kpnl band which frequently suffers $ori_L$-associated deletions upon cloning in bacteria (McGeoch, D. J., et al., *J. Gen. Virol.* 69:1531–1574 (1988); Polvino-Bodnar, M., et al., *J. Virol.* 61:3528–3535 (1987); FIGS. 1E and 2). Moreover, this pattern of restriction fragments was entirely conserved, even after 3 consecutive colony purifications, thereby confirming the structural stability of large single-copy plasmids.

Generation of Infectious HSV-1 From fHSVpac+ DNA Amplified in *E. coli*

Confirming the inventors' hypothesis, fHSVΔpac did not generate HSV-1 progeny virus upon transfection into cells in culture (Table 1). To assess whether the capability of generating replication-competent virus progeny can be restored by inclusion of the pac element in the BAC clone, fHSVpac+ was constructed by inserting the pac signal into the unique PacI site of fHSVΔpac (see, FIG. 2). As shown in Table 1, transfection of 0.2 μg fHSVpac+ DNA gave rise to more than 800 plaques at 2 days after transfection. Higher amounts of DNA produced a complete CPE in the same time period. In contrast, 1.5 μg of DNA from cosmid set C resulted only in an average of 20 plaques, a number similar to that reported by Cunningham, C. and Davison, A. J., *Virology* 197:116–124 (1993).

TABLE 1

Plaque Formation after Transfection of *E. Coli* Clones Representing the HSV-1 Genome

| *E. coli* clones | Amount of transfected DNA (μg) | Number of plaques (2 d p.t.)[a] |
|---|---|---|
| fHSVΔpac | 1.5 | 0 ± 0 |
| cos set C6Δa48Δa | 1.5 | 0 ± 0 |
| fHSVpac+ | 0.2 | 873 ± 164 |
| fHSVpac+ | 0.5 | CPE[b] |
| fHSVpac+ | 1.5 | CPE |
| cos set C | 1.5 | 20 ± 6 |

Cells were transfected as described in the text.
[a]Numbers represent the mean ± SD.
[b]A general CPE was observed. Plaques were too numerous to be counted.

fHSVΔpac-Mediated Packaging of Amplicons Into HSV-1 Virions

Figure 3A:
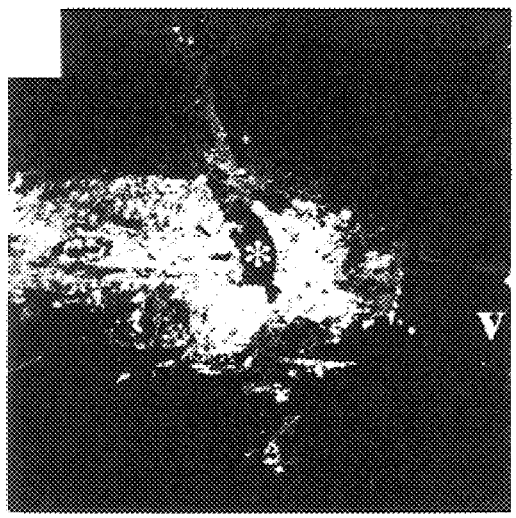
FIGS. 3A–3D are photomicrographs showing GFP-positive cells at day 4 following injection of pHSVGFP amplicon vector, packaged helper virus-free in this system, into rat hippocampus ($7.5 \times 10^5$ t.u., FIGS. 3A and 3B) or liver ($7.5 \times 10^6$ t.u., FIGS. 3C and 3D). Needle tract (*), third ventricle (v), and central vein (cv) are indicated.
Figure 3B:
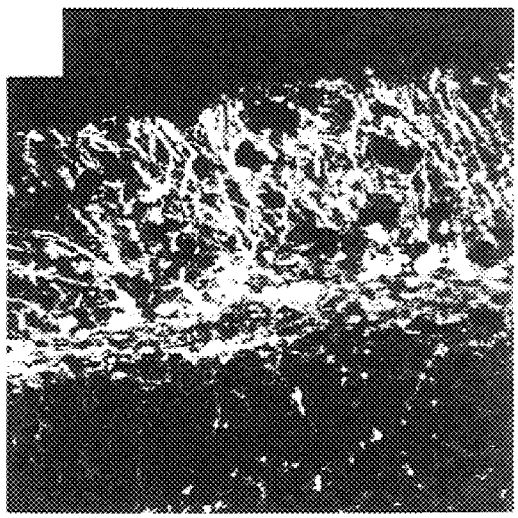
Figure 3C:
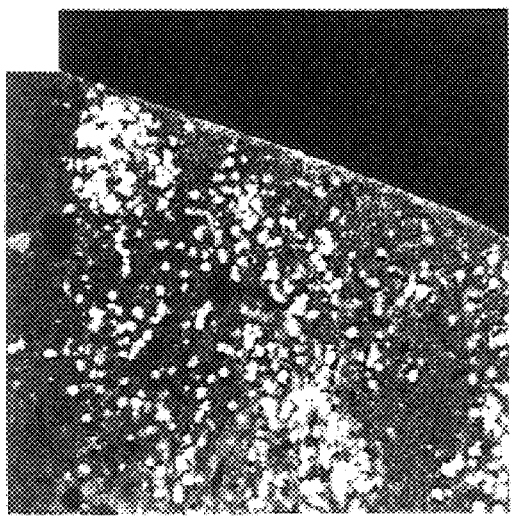
Figure 3D:
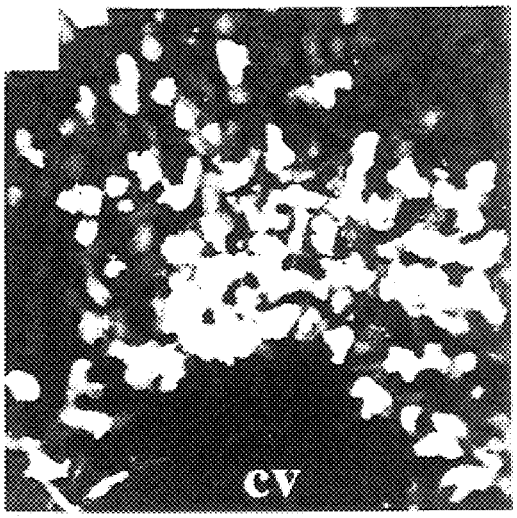

Although fHSVΔpac alone did not generate replication-competent virus progeny, this clone could efficiently package co-transfected pHSVGFP amplicon DNA into HSV-1 virions and generate vector stocks with titers of $8.6 \times 10^{6 \pm 4.0 \times 10^6}$ t.u./ml (mean±STDEV; n=3 experiments). Although the efficiency of plaque formation by fHSVpac+ was more than 400-fold higher than that of cosmid set C (see, Table 1), the amplicon vector titers realized with fHSVΔpac showed only a 2-fold increase compared to cosmid set C6Δa48Δa. This may be due to the limited replication capacity of the amplicon, because preliminary studies indicate that somewhat higher vector titers (two-fold) can be achieved with amplicons containing the SV40 origin of DNA replication in cells transfected with the SV40 T antigen (T. A. Stavropoulos and C. A. Strathdee, personal communication). Because of a sequence homology between fHSVΔpac and pHSVGFP (~1 kb containing $ori_s$ and IE4/5 promoter; Aboody-Guterman, K. S., et al., *NeuroReport* 8:3801–3808 (1997)), which can support the generation of a packageable HSV-1 genome via a single homologous recombination event, the vector stocks were expected to be heavily contaminated by replication-competent virus. However, contamination by such viruses was surprisingly low, with 59±52 PFU/ml (mean±STDEV; n=3 experiments), resulting in a ratio of transducing vector units to replication-competent virus of >1.5×10$^5$. Consequently, the injection of 7.5×10$^5$ t.u. of pHSVGFP vector (along with potentially five replication-competent virus particles) into the hippocampus of rats resulted in thousands of GFP-positive cells in this area with minimal cytotoxic effects on day 4 after injection (FIGS. 3A and B). There was some tissue necrosis, bleeding, and influx of immune cells at the injection site, as is typical for replication defective adenovirus and HSV-1 vectors. The injection of 7.5×10$^6$ t.u. of pHSVGFP vector into the rat liver resulted also in a high percentage of GFP-positive hepatocytes with the minimal cytopathic changes (FIGS. 3C and D). The extent of delivery with these BAC-packaged amplicons appeared similar to helper virus-packaged amplicons.

As a possible explanation for the low amount of contamination with replication-competent progeny virus, a DNA molecule generated via a single crossover between pHSVGFP and fHSVΔpac would be larger than 165 kb and may not be packaged as efficiently as a 152 kb molecule (size of the standard HSV-1 genome), even in the presence of a functional pac signal. However, further developments should be targeted at eliminating any replication-competent progeny virus. The possibility to generate infectious progeny from fHSVΔpac through rescue with the pac signal offers an efficient way of manipulating the large HSV-1 genome for the targeted design of improved HSV-1 vector systems, both recombinant and amplicon. It permits the isolation of recombinant HSV-1 without the need for selection via homologous recombination directly in mammalian cells or in bacteria. If flanked by recognition sites for restriction endonucleases that do not cut HSV-1 DNA, the pac signal can be deleted, and the recombinant genomes can be re-introduced into *E. coli* as BACs to serve as helper DNA for the packaging of amplicons into HSV-1 virions. The strength of the new packaging system is the simplicity: co-transfection of the amplicon plasmid with a single helper BAC plasmid, rather than with five cosmids; the high genomic stability of the BACs, whereas some of the cosmids have proven very unstable; and the ease of introducing mutations into the BACs which will decrease cytotoxicity, and hopefully increase titers, as compared to more complicated manipulations required for the cosmids.

EXAMPLE 2

Currently, there are three safety features designed in the packaging vector fHSVΔpac that guard against the potential risk of helper virus contamination. These include:

1) Inactivated pac signals in the HSV-1 helper genome;
2) Inactivation of both copies of the $\gamma_1$34.5 (RL1) gene; and
3) Contaminating helper viruses are sensitive to ganciclovir treatment due to the functional TK gene.

In addition to these features, it was theorized that inactivation of an essential gene in the helper genome, as well as an increase in size of the helper plasmid, might further reduce the risk of helper virus contamination from amplicons packaged with HSV-BAC. The Applicants note that the term "helper plasmid" used herein is intended to be used synonymously with the term "packaging vector," described supra.

Targeted Disruption of the ICP27 Gene From fHSVΔpac

Figure 4:
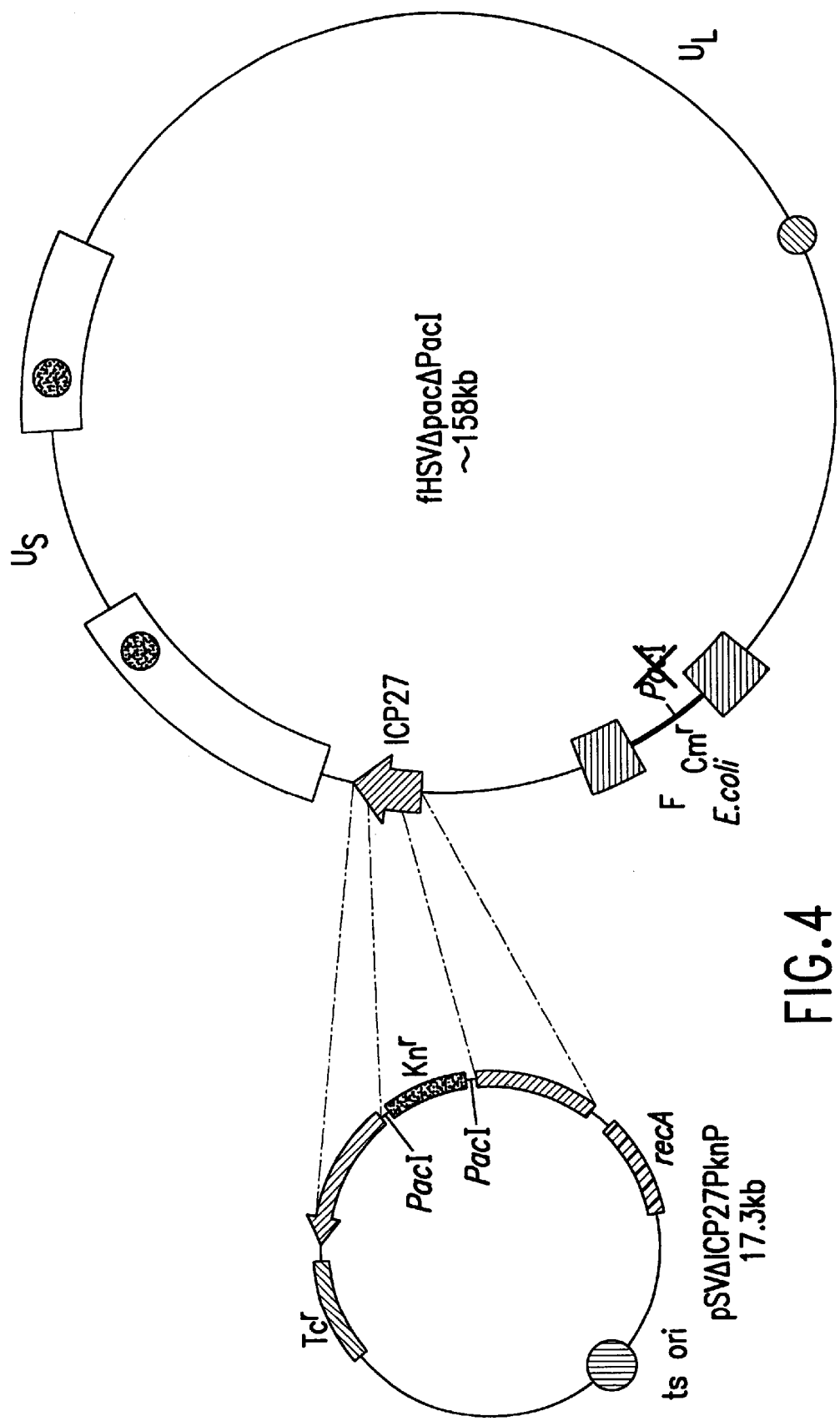
FIG. 4 depicts schematically the targeted disruption of the ICP27 gene from fHSVΔpac by RecA-mediated homologous recombination in *E. coli*.

The gene that was targeted for deletion from fHSVΔpac was ICP27. ICP27 is a gene essential for HSV replication. This was accomplished in *E. coli* by recA-mediated homologous recombination, as illustrated in FIG. 4.

First, the ICP27-targeting plasmid, pSVΔICP27PknP, was designed, which has a temperature sensitive origin of replication, tetracycline-resistant gene, *E. coli* recA gene, and kanamycin-resistant gene flanked by the ICP27 homologous recombination sequences. This targeting plasmid was electroporated into bacteria containing fHSVΔpacΔPacI, which was generated from fHSVΔpac by inactivating the PacI site through adopter ligation.

Figure 5:
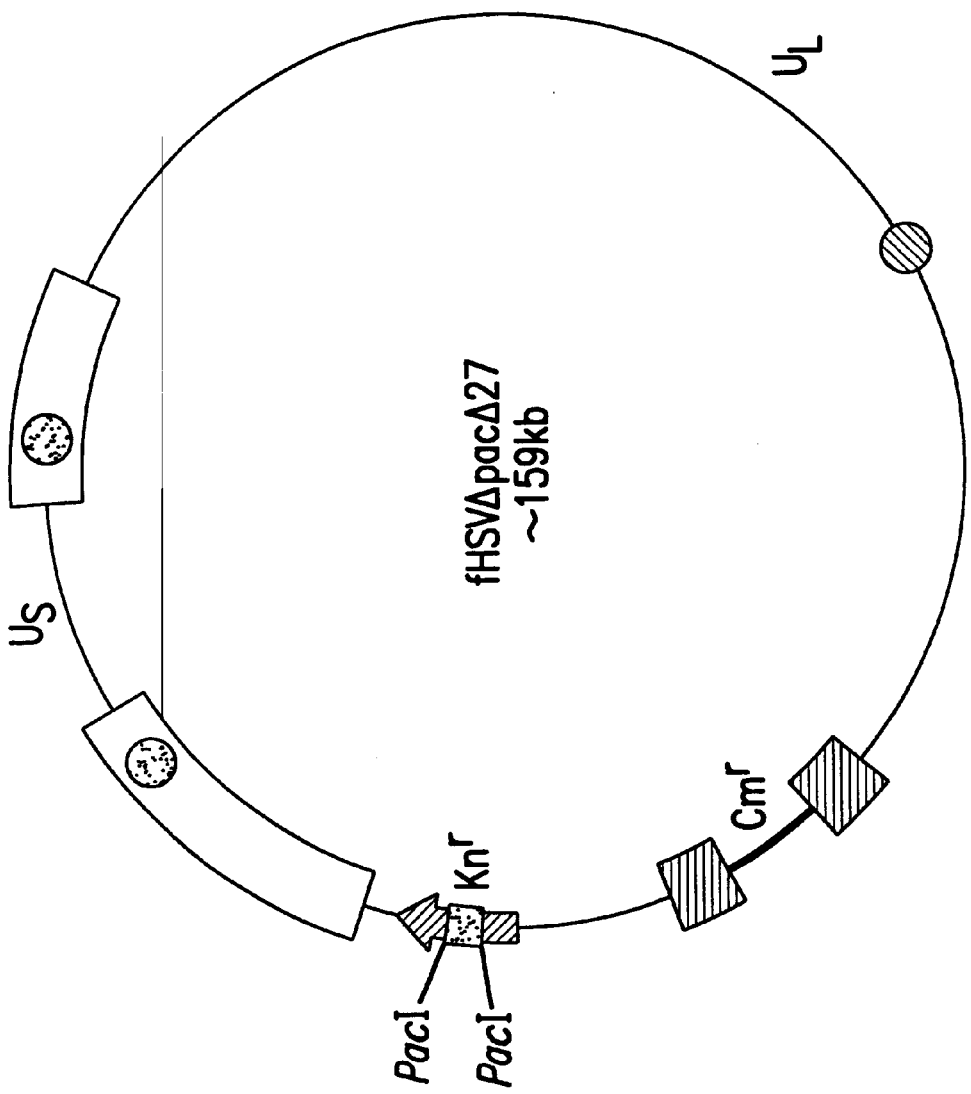

Next, clones were selected for chloramphenicol and kanamycin resistance as well as tetracycline sensitivity at the non-permissive temperature, 43 degrees. As a result, a clone, fHSVΔpac27, was isolated (FIG. 5), which has a deletion in the ICP27 gene; the deletion has been replaced by a kanamycin-resistant gene flanked by two PacI sites.

The amplicon titers obtained with this clone as a helper were as follows: When packaged on VERO cells, no detectable vector was obtained. With 2-2 cells (which are the VERO cells stably transfected with ICP27), however, a vector titer of 2.7×10$^3$ t.u./ml was obtained.

In creasing the Size of the HSV-1 Helper Plasmid

The second strategy that was employed to minimize helper virus regeneration was to increase the size of the fHSVΔpac. This strategy was based on the observations shown in Table 2.

TABLE 2

Increasing the Size of the Amplicon Decreases the Chance of Regeneration of the Helper Virus from fHSV Δpac.

| Amplicon | Vector titers[a] (TU/ml) | Helper virus titers[b] (PFU/ml) | Vector/helper ratio (TU/PFU) |
|---|---|---|---|
| pHSVGFP (5.6 kb) | 5.0 × 10$^6$ | 150 | 3.3 × 10$^4$ |
| pHGCXLuc (9.4 kb) | 4.0 × 10$^6$ | 61 | 6.6 × 10$^4$ |
| pREHGCaLuc (14.3 kb) | 3.5 × 10$^6$ | 6.7 | 5.2 × 10$^5$ |

[a]Titers of amplicon vectors were determined on 293 cells by counting GFP positive cells under a fluorescent microscope.
[b]Titers of replication-competent virus were determined on VERO cells by counting plaques 7 days after infection. These experiments were repeated three times and the means of each data are shown.

When amplicons of increased size were packaged, a decrease in the number of helper virus titers was observed. For example, packaging an amplicon of 14.3 kb generated 22 times less helper virus than when an amplicon of 5.6 kb was used. This data shows that adding extra DNA sequence(s) to the amplicon to be packaged could reduce the risk of helper virus regeneration.

Figure 6:
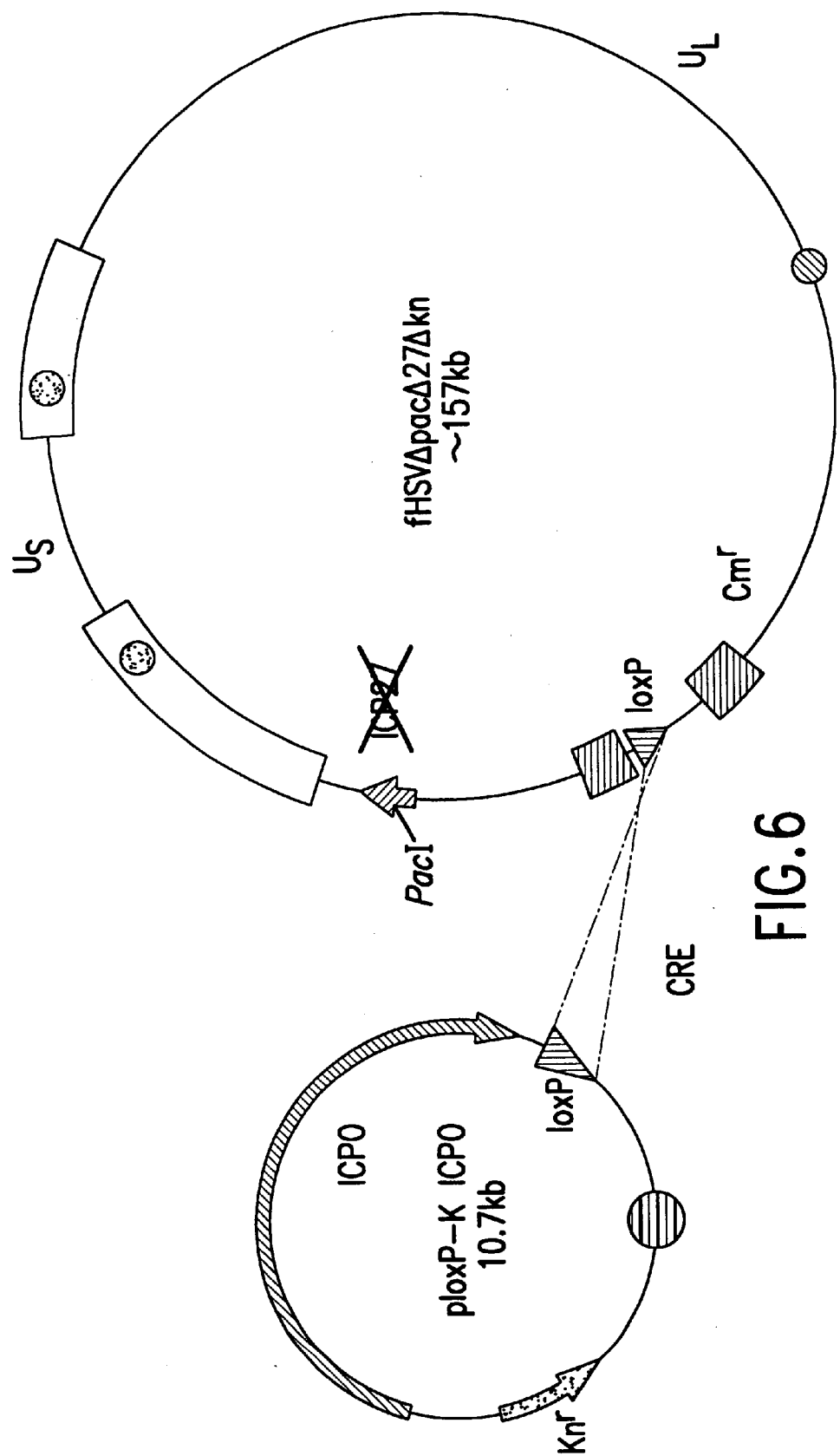
FIG. 6 depicts schematically how the size of fHSVΔpacΔ27 can be increased through CRE-mediated site-specific recombination.
Figure 7:
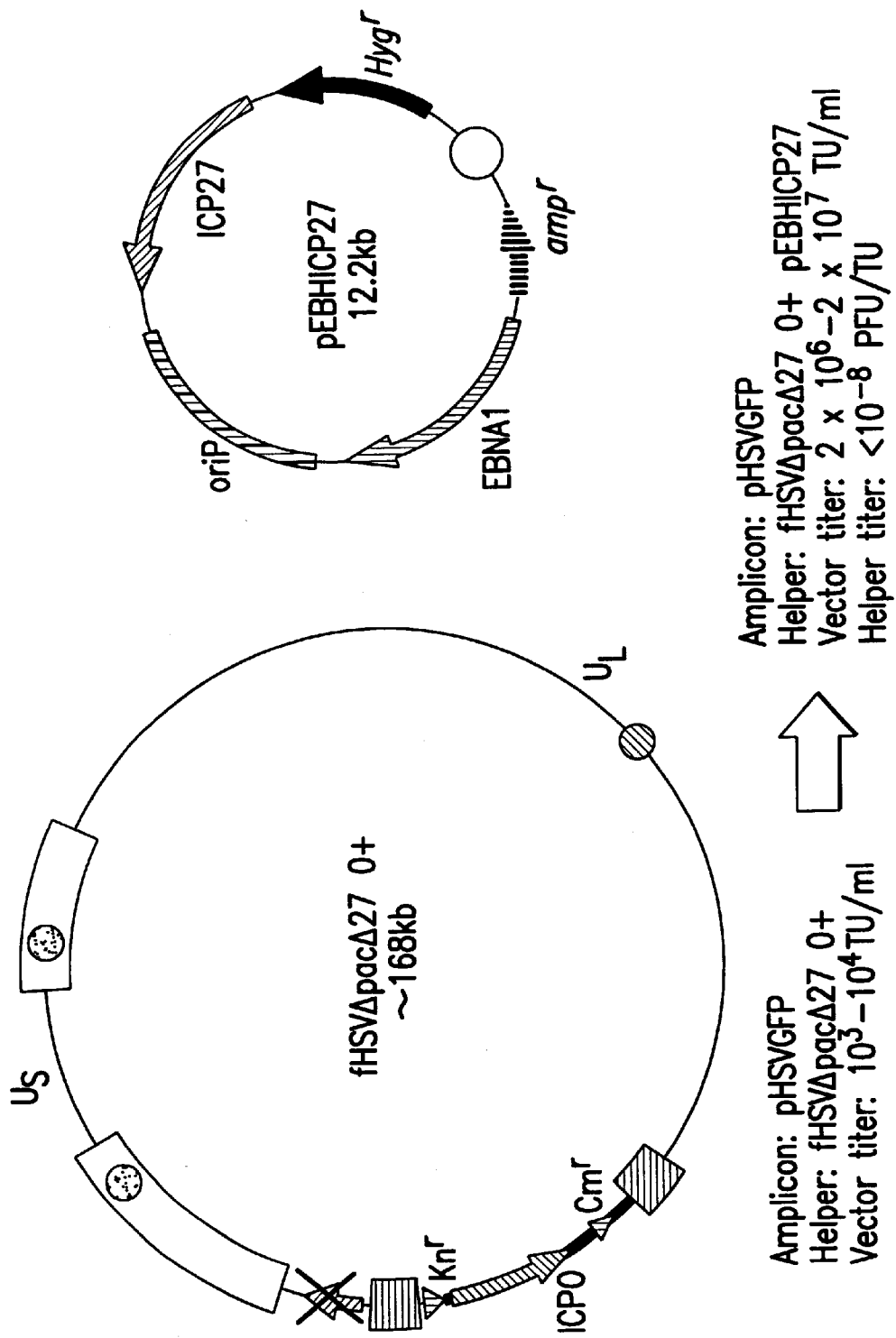
FIG. 7 depicts schematically the packaging of HSV-1 amplicons using fHSVΔpacΔ27 0+ as helper virus.

First, the kanamycin-resistant gene was removed from the fHSVΔpacΔ27, by PacI digestion followed by self-ligation. By taking advantage of the presence of a loxP site in the BAC backbone, a 10.7-kb DNA fragment containing ICP0 gene was inserted into this clone, using CRE recombinase (FIG. 6). As a result, a 168-kb clone was isolated, having an additional copy of ICP0. The clone was called fHSVΔpacΔ27 0+ (FIG. 7).

As shown before, transfection of this clone alone with the amplicon generated relatively low titers in 2-2 cells. However, addition of ICP27 expressing plasmid in the transfection mixture produced a significant increase in the titers of amplicon, up to $2 \times 10^7$ t.u./ml.

Even more significantly, the combination of: (1) deleting the ICP27 gene; and (2) increasing the size of the helper plasmid, resulted in the elimination of helper virus regeneration, at least to a level of $10^{-8}$ PFU per TU of vector.

In conclusion, recA-mediated homologous recombination and CRE-mediated site-specific insertion can be used to modify the HSV-1 helper BAC clones. Minimization of helper virus regeneration was accomplished by: removing ICP27 from the fHSVΔpac and trans-complementation of ICP27 with a separate plasmid; and increasing the size of the BAC clone beyond the packaging capacity of HSV-1.

EXAMPLE 3

Introduction

The immune system reacts to most systemic infections with broad and vigorous cytokine, cellular and humoral responses that restrict spread of the infectious agent within the organism. For example, within days after primary infection with herpes simplex virus type 1 (HSV-1), the immune system induces a variety of cytokines, chemokines, adhesion molecules, natural killer cells, macrophages, γ/δ T-cells, CD4⁻ and CD8⁺ T-cells, and produces neutralizing antibodies (Kapoor, A. K., et al., *Immunol Lett* 5:259–265 (1982); Jennings, S. R., et al., *Cell Immunol* 133:234–252 (1 991); Valyi-Nagy, T., et al., *J. Virol* 66:7336–7345 (1992); Lopez, Z., et al, in *The Human Herpesviruses*, Roizman, et al., eds., Raven, N.Y. (1993), pp. 397–425; Smith, P. M., et al., *Virology* 202 :76–88 (1994); Manickan, E. & Rouse, B. T., *J. Virol* 69:8178–8179 (1995); Liu, T., et al., *J. Virol* 70:264–271 (1996); Hendricks, R. L., *Cornea* 16:503–506 (1997); Posavad, C. M., et al., *Nat Med* 4:381–382 (1998); Grob, P., et al., *J. Virol*, in press, (1999)).

Anti-viral vaccines, which have been around for at least two centuries, are modified target agents designed to reduce pathogenicity but conserve immunogenicity. Modified live virus (mlv) vaccines are based on either attenuated or replication-defective viruses and induce an immune response comparable to that induced by the parent viruses. Although biologically much safer, inactivated virus-vaccines and subunit vaccines are much less effective in inducing immune responses than mlv vaccines, indicating a link between some elements of virus replication and immunogenicity (Morrison, L. A. & Knipe, D. M., *J. Virol* 68:689–696 (1994); Ghiasi, H., et al., *Vaccine* 14:107–112 (1996); Siegrist, C. A., et al., *Vaccine* 16:1473–1478 (1998)).

In recent years, the use of naked DNA for immunization stirred great hopes for the development of safe and efficient vaccines (Fynan, E. F., et al., *Proc Natl Acad Sci USA* 90:11478–11482 (1993); Robinson, H. J. & Torres, C. A., *Semin Immunol* 9:271–283 (1997)). As opposed to the purified proteins used as subunit vaccines, immunization with antigen-encoding DNA supports protein synthesis in host cells, thereby activating the cellular arm of the immune system (Porgador, A., et al., *J Exp Med* 188:1075–1082 (1998); Akbari, O., et al., *J Exp Med* 189:169–178 (1999)). However, the plasmid vectors previously used for vaccinations did not have the capacity to hold the wide range of antigens needed to induce broad immune responses against complex (viral) pathogens (Manickan, E., et al., *J. Immunol* 155:259–265 (1995); Ghiasi, H., et al., *Antiviral Res* 28:147–157 (1995); Hriharan, M. J., et al., *J. Virol* 72:950–958 (1998)). Live virus vaccines, on the other hand, are not entirely safe and, moreover, are not easily manipulated to counter the complicated interplay of the virus with the host's defense system.

Based on bacterial artificial chromosomes (BAC), the inventors have established a vaccination strategy ("BAC-VAC"), using HSV-1 as an example. BAC-VAC allows replicative amplification of the vaccine DNA in the host cell nucleus and combines safety and simplicity of DNA vaccines with the high immunogenicity of live-virus vaccines. BACs have been widely used in genome research because of their capacity to accommodate large inserts (>300 kb) and their genetic stability in bacteria (O'Connor, M., et al., *Science* 244:1307–1312 (1989); Shizuya, H., et al., *Proc Natl Acad Sci USA* 89:8794–8797 (1992)). BACs are also suitable for cloning the large genomes of DNA viruses, as first demonstrated by Luckow et al. (Luckow, V. A., et al., *J. Virol* 67:4566–4579 (1993)) with baculovirus (130 kb).

Recently, the genomes of several herpesviruses, including those of murine cytomegalovirus (230 kb), Epstein-Barr virus (170 kb), and HSV-1 (152 kb) have successfully been cloned in *E. coli* where they are stably maintained as supercoiled plasmid DNA and accessible to the prokaryotic tools for modification (Messerle, M., et al., *Proc Natl Acad Sci USA* 94, 14759–14763 (1997); Delecluse, H. J., et al., *Proc Natl Acad Sci USA* 95:8245–8250 (1998); Saeki, Y., et al., *Hum Gene Ther* 9:2787–2794 (1998); Stavropoulos, T. A. & Strathdee, C. A., et al., *J. Virol* 72:7137–7143 (1998)). Upon transfection into mammalian cells, these plasmids can efficiently mediate the production of infectious virus progeny.

To explore the potential usefulness of BACs for vaccination protocols, the inventors chose a plasmid containing a replication-competent but packaging-defective HSV-1 genome (fHSVΔpac) developed by Saeki et al., supra; and described above in Example 1. The HSV-1 DNA cleavage/ packaging signals (pac), which are essential for cleavage of the concatemeric products of viral DNA replication into unit-length genomes and their subsequent packaging into virions, were excluded, to prevent the formation of HSV-1 progeny from the BAC DNA. Id. Although packaging-defective in mammalian cells, fHSVΔpac can still replicate, express the HSV-1 genes, cause cytotoxic effects, produce non-infectious, virus-like particles, and support the packaging of co-transfected HSV-1-based amplicon vectors into virions (Luckow, et al., supra; Saeki, et al., supra). These functions mimic an entire lytic cycle of the HSV-1 infection and, consequently, immunization with fHSVΔpac DNA should exert all of the immunomodulatory functions considered important for efficient immune stimulation (Grob, et al., supra; Siegrist, et al., supra).

The experiments described in this Example demonstrate that small amounts of the prototype BAC-VAC, fHSVΔpac, can induce broad immune responses able to protect mice from intracerebral (i.c.) challenge with wild-type (wt) HSV-1 at a dose of at least 200 $LD_{50}$. BAC-VACs, per se, or in combination with genetic elements that support replicative amplification of the DNA in the cell nucleus, represent a useful new generation of DNA-based vaccination strategies for many viral and non-viral antigens.

Materials and Methods
Animals, Cells, and Viruses

Female, 7–10 week-old C57BL/6 (H-$2^b$) or 129Sv/Ev (H-$2^b$) mice were bred and maintained in specific pathogen free conditions at the Walter and Eliza Hall Institute for Medical Research (Victoria, Australia). VERO cells (ATCC, Manassas, Va.), HSV-1 glycoprotein H (gH)-expressing VERO cells (F1; Delecluse, H. J., et al., *Proc Natl Acad Sci USA* 95:8245–8250 (1998); McLean, C. S., et al., *J Infect Dis* 170:1100–1109 (1994)), H-$2^b$ thymoma cells (EL-4), and glycoprotein B (gB)-expressing fibroblast cells (MC57; Vasilakos, J. P. & Michael, J. G., *J Immunol* 150:2346–2355 (1993); Cose, S. C., et al., *J. Virol* 69:5849–5852 (1995)) were grown in complete Dulbecco's modified minimal essential medium (DMEM) supplemented with 10% fetal bovine serum (FSB). HSV-1 strain F was obtained from Dr. B. Roizman (University of Chicago) and propagated on VERO cells (Ejercito, P. M., et al., *J. Gen Virol* 2:357–364 (1968)). Disabled infectious single cycle (DISC) HSV-1, a gH deletion-mutant capable of completing a single cycle of infection, was kindly provided by Dr. J. Shields (Cantab Pharmaceuticals, Cambridge, UK) and was propagated on F1 cells (Delecluse, H. J., et al., supra; McLean, C. S., et al., supra). HSV-1 amplicon pHSVGFP, which expresses the gene for green fluorescent protein (GFP), was packaged into HSV-1 virions by using the helper virus-free method (Fraefel, C., et al., *J. Virol* 70:7190–7197 (1996); Aboody-Guterman, K. S., et al., *NeuroReport* 8:3801–3808 (1997);

Fraefel, C., in *Current Protocols in Neuroscience*, Crawley, et al., eds., John Wiley & Sons, Inc., New York, N.Y. (1999), pp. 4.14.1–4.14.16).
Vaccine DNA The cloning of the 152 kb HSV-1 genome, with DNA cleavage/packaging signals (pac) excluded, as a BAC in *E. coli* (fHSVΔpac), has been described in Saeki, Y., et al., *Hum Gene Ther* 9:2787–94 (1998) and Example 1. Supercoiled fHSVΔpac DNA was isolated by alkaline lysis and Tip-500 column chromatography (Quiagen, Chatsworth, Calif.), and purified by cesium chloride equilibrium centrifugation. Plasmid psOVA DNA, which encodes a secreted form of chicken ovalbumin, was used as control (Boyle, et al., *Int Immunol* 9:1897–906 (1997)). DNA preparations of fHSVΔpac and psOVA contained <100 units of endotoxin per mg as determined by the limulus amoebocyte lysate assay (Boyle, et al., *Proc Natl Acad Sci USA* 94:14626–31 (1997)).

Immunization and Virus Challenge Protocols
Intradermal (id.) Injection

Mice were immunized i.d. at the base of the tail either with 50 μg DNA in 70 μl saline, or, as a control, with $10^9$ plaque forming units (PFU) of DISC HSV-1 in 100 μl saline (Boyle, J. S., et al., *Proc Natl Acad Sci USA* 94:14626–14631 (1997); Aboody-Guterman, K. S., et al., supra). Two weeks later, the animals were boosted with the same amount of DNA or virus and, 10 days later, were analyzed for the induction of cellular and humoral immune responses or challenged with wt HSV-1.
Gold-Particle Bombardment DNA was adsorbed to gold-particles (1 μm) and delivered i.d. at the base of the tail by gold-particle bombardment using a gene gun as recommended by the manufacturer (Bio-Rad). The animals received two doses of 750 ng DNA each per immunization. Booster immunizations were given every 2 weeks using the same amount of DNA. Ten days after each immunization, groups of animals were analyzed for the induction of HSV-1-specific cytotoxic T lymphocytes (CTL) and antibody responses, or challenged with wt HSV-1.
Virus Challenge Mice were anesthetized with ether and injected intracerebrally (i.c.) with $2 \times 10^5$ PFU of HSV-1 strain F in 10 μl phosphate buffered saline (PBS). The dose of HSV-1 that causes lethal infections in 50% of the animals ($LD_{50}$) has been determined in age matched C57BL/6 mice and was $10^2$–$10^3$ PFU. The animals were examined daily for signs of disease, and the surviving animals were counted 14 days after the challenge.
Serum Transfer Serum prepared from pooled blood of fHSVΔpac-immunized or DISC HSV-1-immunized mice was analyzed for HSV-1-specific neutralizing antibodies and transferred intravenously (100 μl) or intraperitoneally (1 ml) into naive mice. After 4 hours, the animals were challenged with HSV-1 as described above, and sera were collected from some of the mice to determine post-transfer neutralizing antibody titers.
Assessment of gB-Specific CTL Activity Spleen cells or lymph node cells were isolated from immunized or control animals and assayed directly, or after restimulation in vitro for 5 days by using irradiated HSV-1 gB-expressing MC57 cells, for reactivity against EL-4 cells (Vasilakos, J. P. & Michael, J. G., *J Immunol* 150:2346–2355 (1993); Cose, S. C., et al., *J. Virol* 69:5849–5852 (1995); Salvucci, L. A., et al., *J. Virol* 69:1122–1131 (1995)). EL-4 target cells were pulsed for 1 hour with 3 μg/ml of gB-specific H-$2^b$ restricted peptide SSIEFARL (single letter amino acid code) (SEQ ID NO:2) and analyzed by a standard 4-hour $^{51}$Cr release cytotoxicity assay. An overnight (15-hour) $^{51}$Cr release cytotoxicity assay was used when effector cells were analyzed directly without in vitro restimulation. Spontaneous release was consistently below 15% in a 4-hour assay and approximately 25% in overnight assays.
Flow Cytometry Splenocytes or lymph node cells were analyzed by flow cytometry (Becton Dickinson) for the presence of CD8$^+$ T-cells (antibody 500-A2, Caltag, Burlingame, Calif.) carrying the T cell receptor (TCR) Vβ10 (antibody B21.5; Pharmingen, San Diego Calif.) (Boyle, J. S., et al., *Int Immunol* 9:1897–1906 (1997)) which is typically present in increased numbers after HSV-1 infections (Cose, S. C., et al., *J. Virol* 69:5849–5852 (1995); Jones, C. M., et al., *Int Immunol* 9:1319–1328 (1997)).
Serology ELISA was performed and antibody titers were determined as previously described (Boyle, J. S., et al., *Int Immunol* 9:1897–1906 (1997)) by using peroxidase-conjugated polyclonal anti mouse IgG1, IgG2a, IgG2b, and IgG3 antibodies (Southern Biotechnology Associates). HSV-1 antigen was prepared from virus-infected VERO cells and titered for optimal performance in ELISA (Knuchel, M., et al., *Vet Microbiol* 32:117–134 (1992)). Sera collected from immunized and control animals were analyzed for HSV-1 neutralization using standard methods.
Western Immunoblot Analysis Radioactively labeled cell lysates were prepared, subjected to SDS polyacrylamide gel electrophoresis (SDS/PAGE), transferred to nitrocellulose, and immunostained essentially as described (Ackermann, M., et al., *J. Virol* 52:108–118 (1984)). Briefly, monolayers of Hep-2 cells were infected with either HSV-1 (strain F) or HSV-2 (strain G) at a multiplicity of infection of 20 PFU per cell, or mock-infected and labeled with [$^{35}$S]-methionine from 16 to 20 hours post infection. The cells were lysed in SDS buffer, and the proteins were separated on a 9.25% SDS-polyacrylamide gel, cross-linked with N,N'-diallyltartardiamide, blotted to nitrocellulose, and visualized by autoradiography. For immunostaining, the nitrocellulose sheet was incubated for 1 hour at 37° C. in blocking solution (25% horse serum, 0.5% NP-40, in PBS). Serum (diluted 1:500 in a solution consisting of 1 volume blocking solution and 2 volumes of PBS) was added and incubated over night at 4° C. Detection was carried out by using the Vectastain ABC Kit and biotinylated anti-mouse IgG as a secondary antibody, avidin and peroxidase-labeled biotin, according to the instructions provided by the manufacturer (Vector Laboratories).

Results and Discussion

Figure 8A:
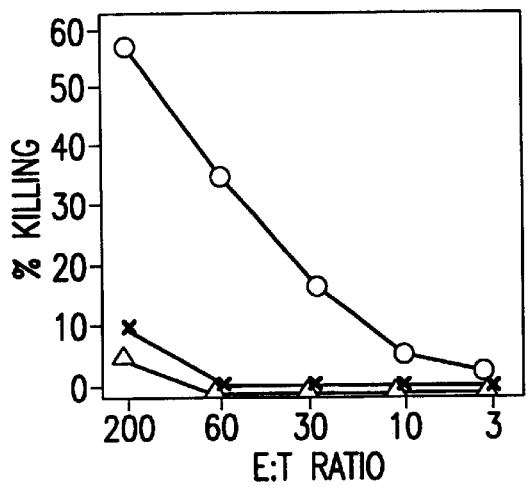
FIGS. 8A–8C depict graphs showing gB-specific CTL-activities of splenocytes (8A, 8B) or lymph node cells (8C).

Intradermal Injection of fHSVΔpac DNA Induces HSV-1-Specific CTL and Antibody Responses In a first set of experiments, mice were injected i.d. with fHSVΔpac (FIG. 1E) or psOVA DNA, as described above in Materials and Methods. Two weeks after each injection, splenocytes or lymph node cells were isolated to analyze CTL activity, and blood was collected to determine HSV-1-specific antibodies. The isolated splenocytes were restimulated for five days by using irradiated HSV-1 glycoprotein B (gB)-expressing MC57 cells, and cytotoxic activity was analyzed by $^{51}$Cr release by using peptide-loaded EL-4 target cells. HSV-1 gB was chosen for this assay because it includes the dominant CTL epitope for the H-2$^b$ haplotype of C57BL/6 mice (Bonneau, R. H., et al., *Virology* 195:62–70 (1993)). FIG. 8A represents one of six experiments and shows specific lysis of the target cells by the restimulated effector cells from fHSVΔpac DNA, but not from psOVA control DNA-immunized mice. Direct CTL activity without restimulation of the isolated splenocytes or lymph node cells could not be detected. A low, but significant, amount of HSV-1-specific antibody was produced after two DNA immunizations, as determined by ELISA (data not shown). The animals were not protected from lethal intracerebral (i.c.) HSV-1 infection, even after three immunizations with fHSVΔpac (data not shown).

Other investigators have demonstrated that administration of DNA by gold-particle bombardment is 10- to 100-fold more effective for the induction of immune responses than direct i.d. injection (Robinson, H. L., & Torres, C. A., *Semin Immunol* 9:271–283 (1997); Pertmer, T. M., et al., *Vaccine* 13:1427–1430 (1995)). The method of DNA transfer may be even more critical for large DNA molecules, such as the 158 kb plasmid fHSVΔpac. The following experiment was performed to address this point.

Immunizing Mice Once with fHSVΔpac DNA by Gold-Particle Bombardment Induces Strong CTL Activity After In Vitro Restimulation Mice were primed with 1.5 μg of fHSVΔpac DNA delivered i.d. by gold-particle bombardment, and the immune responses were compared with those induced by i.d. injection of 50 μg of fHSVΔpac DNA (see above), or infection with either 10$^4$ to 10$^9$ PFU of DISC HSV-1 or 10$^6$ t.u. of helper virus-free HSV-1 amplicon vector pHSVGFP. DISC HSV-1 can complete one cycle of replication without producing infectious progeny virus (McLean, C. S., et al., *J. Infect Dis* 170:1100–1109 (1994)) and was used as standard modified live virus in all forthcoming experiments. HSV-1 amplicon vectors are replication defective, do not express any viral genes, but contain all structural components of HSV-1 particles (Fraefel, C., et al., *J. Virol* 70:7190–7197 (1996)).

Figure 8B:
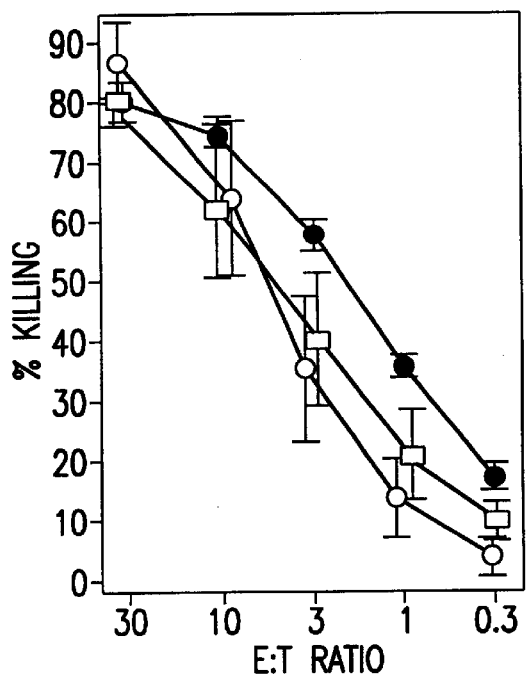

One or two weeks after a single vaccination, splenocytes were harvested and analyzed for HSV-1 gB-specific CTL activity after in vitro restimulation. The results are shown in FIG. 8B and can be summarized as follows: A single immunization with 1.5 μg of fHSVΔpac DNA by gold-particle bombardment was far more effective in inducing CTL activity than two i.d. injections with 50 μg of DNA from the same batch. A similarly high gB-specific CTL activity was induced after immunization with 10$^9$ PFU of DISC HSV-1, which decreased with smaller amounts of virus in a dose-dependent manner. Immunization with psOVA DNA or with 10$^6$ t.u. of HSV-1 amplicon vector did not result in detectable CTL activity against gB (FIGS. 8A and 8B). However, restimulated splenocytes from psOVA immunized mice revealed cytotoxic activity when assayed against the OVA peptide 257–264 (Hogquist, K. A., et al., *Cell* 76:17–27 (1994)).

The next experiments aimed to further characterize the fHSVΔpac-induced CTL response and to determine whether CTL activity was detectable without in vitro restimulation of splenocytes or lymph node cells. DNA immunizations were performed by gold-particle bombardment in all further experiments.

CTLs from fHSVΔpac DNA-Immunized Mice have an Increased Frequency of the T Cell Receptor Vβ10

Figure 9:
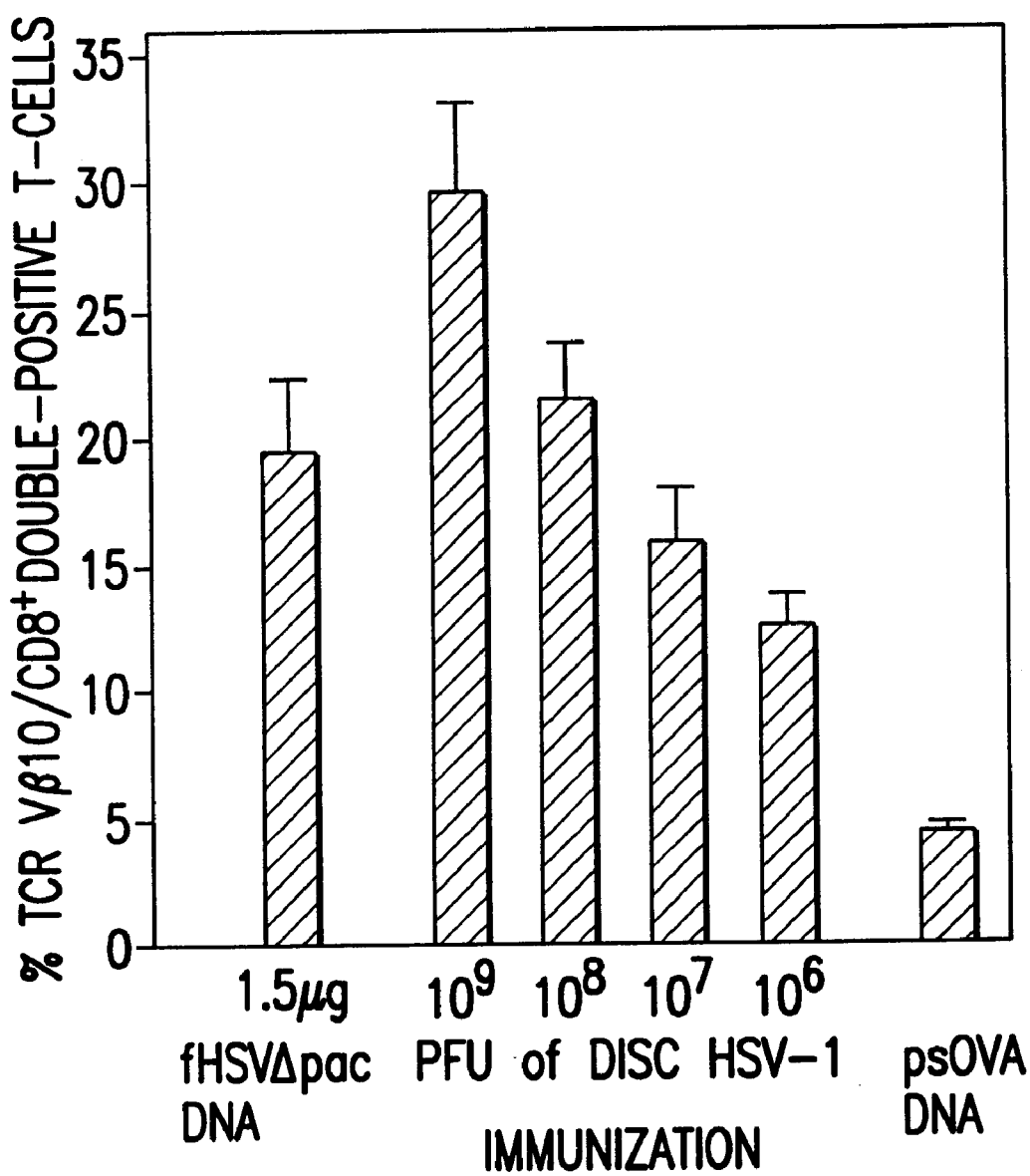
FIG. 9 is a bar graph showing TCR Vβ10/CD8$^+$ double-positive T-cells. Mice (three per group) were immunized with 1.5 μg fHSVΔpac DNA by gold-particle bombardment, or with $10^9$, $10^8$, $10^7$ or $10^6$ PFU of DISC HSV-1 by infection. Ten days after the immunizations, splenocytes were harvested, restimulated in vitro for 5 days, and then analyzed by fluorescence-activated cell sorting (FACS). The numbers indicate the ratios of TCR Vβ10 and CD8$^+$ double-positive T-cells to the total numbers of CD8$^+$ T-cells×100%. Restimulated splenocytes from psOVA DNA-immunized mice served as control.

A single H-2$^b$ restricted peptide of gB is a major target for CTL cell lines or T-cells freshly isolated from draining lymph nodes of HSV-1 infected C57BL/6 mice (Vasilakos, J. P. & Michael, J. G., *J Immunol* 150:2346–2355 (1993)). These T-cells are CD8$^+$ and express a highly conserved T cell receptor (TCR) Vβ10/junctional sequence combination that can be recognized by a TCR Vβ10-specific monoclonal antibody (Cose, S. C., et al., *J. Virol* 69:5849–5852 (1995); Jones, C. M., et al., *Int Immunol* 9:1319–1328 (1997); Cose, S. C., et al., *Eur J Immunol* 27:2310–2316 (1997)). Fluorescence-activated cell sorting (FACS) analysis of the spleen cells from fHSVΔpac DNA-immunized mice showed that 20%–30% of the cells expressed TCR Vβ10 after restimulation (FIG. 9). In vitro restimulated splenocytes from mice immunized with 10$^6$–10$^9$ PFU of DISC HSV-1 also contained significant numbers of TCR Vβ10 expressing CD8$^+$ T-cells (FIG. 9). Similar results were also obtained in 129Sv/Ev (H-2$^b$) mice immunized with either fHSVΔpac DNA or DISC HSV-1 (data not shown). The presence of TCR Vβ10 and CD8$^+$ double-positive T-cells specific against a single H-2$^b$ restricted peptide of gB after immunization with fHSVΔpac DNA indicates an immunodominance of gB over the other HSV-1 (glyco)proteins that resemble infection with wt HSV-1 or DISC HSV-1. The i.d. injection of 10$^6$ t.u. of HSV-1-amplicon vector, which was used as a control because it does not express any HSV-1 genes, did not induce detectable levels of CTL activity (FIG. 8B) and no HSV-1-specific antibodies. Moreover, the population of TCR Vβ10 and CD8$^+$ double-positive T-cells among the restimulated splenocytes was approximately 5%, similar to splenocytes from control mice (FIG. 9). These results are consistent with earlier experiments that had indicated that infusion of helper virus-free HSV-1 amplicon vector into mouse liver supported the long-term expression of the transgene without causing apparent inflammatory reactions (Fraefel, C., et al., *Mol Med* 3:813–825 (1997)).

Figure 8C:
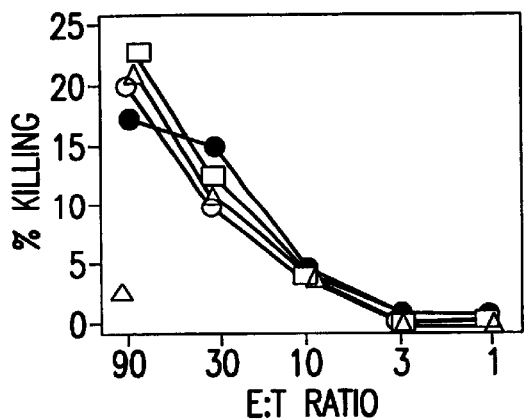

Primary CTL-Response by Lymph Node Cells from Mice Immunized Twice with fHSVΔpac DNA Lymph node cells and spleen cells from mice vaccinated with a single dose of fHSVΔpac DNA were analyzed for direct CTL activity on gB peptide-loaded EL-4 target cells. CTL activity could not be detected in both cell populations without in vitro restimulation, and the number of TCR Vβ10 and CD8+ double-positive T-cells was similar to that of the control animals (data not shown). To determine whether primary CTL activity is detectable after two immunizations, mice were primed with either 1.5 μg of fHSVΔpac DNA or $10^9$ PFU of DISC HSV-1 and, after 14 days, boosted with the same amount of DNA or DISC virus. Ten days after the booster immunizations, significant primary CTL activity was found in lymph node cells draining the site of DNA or virus inoculations (FIG. 8C). In addition, the number of TCR Vβ10 and CD8+ double-positive T-cells in the lymph node cell population was 5%–10% higher than that of control mice (data not shown). Hence, mice immunized with fHSVΔpac DNA or DISC HSV-1 responded with CD8+ T-cells expressing TCR Vβ10, similar to animals infected with replicating wt HSV-1 (Cose, S. C., et al., . *J. Virol* 69:5849–5852 (1995); Jones, C. M., et al., *Int Immunol* 9:1319–1328 (1997); Cose, S. C., et al., *Eur J Immunol* 27:2310–2316 (1997)).

Immunization with fHSVΔpac DNA Induces the Production of Antibodies of all IgG Isotypes and Against a Variety of HSV-1-Specific Proteins C57BL/6 mice were immunized once with 1.5 μg of fHSVΔpac DNA by gold-particle bombardment or with $10^9$ PFU of DISC HSV-1 by infection. ELISA data of the sera analyzed 14 days later showed that DNA immunization resulted in significant HSV-1-specific antibody titers that were, however, 20- to 30-fold lower than those obtained after DISC HSV-1 infection (Table 3).

Figure 10:
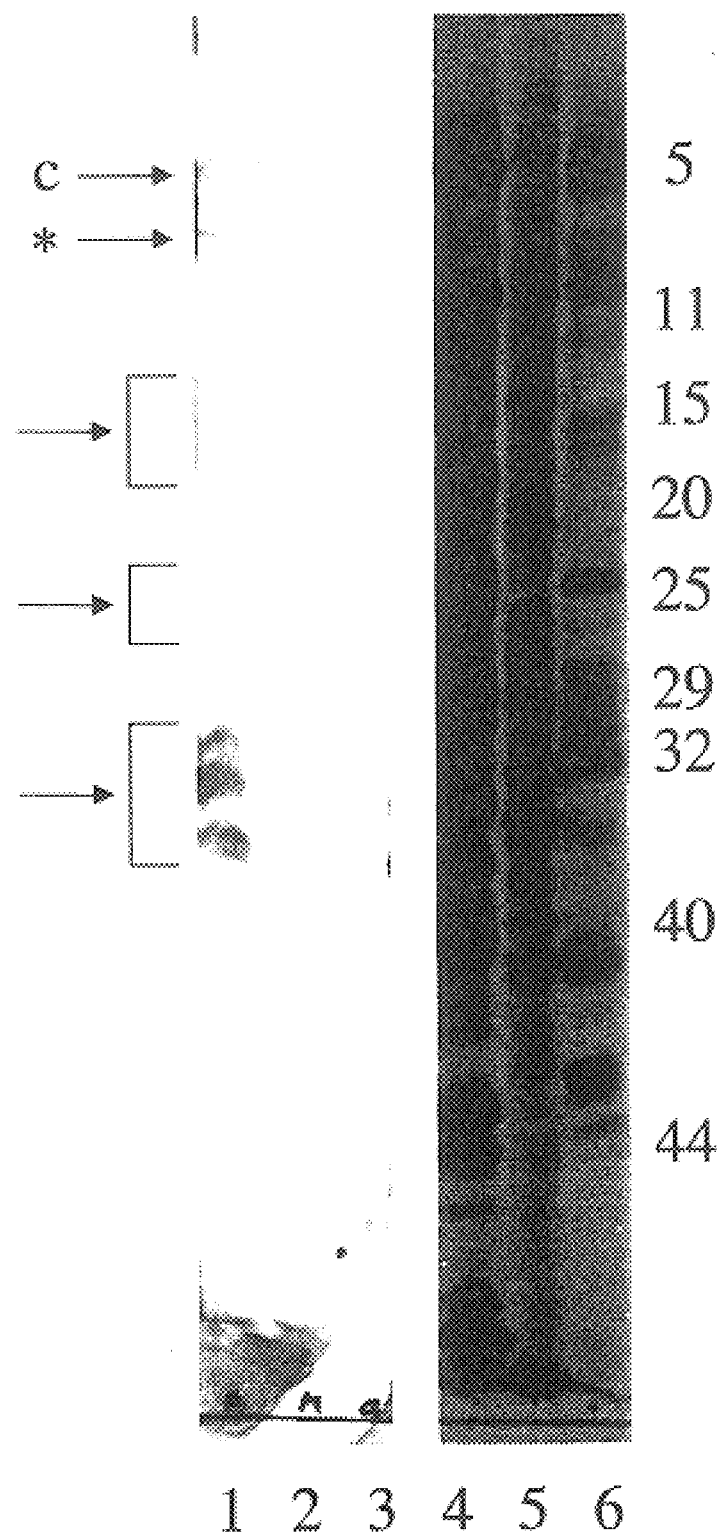
FIG. 10 is an immunoblot of HSV-1 and HSV-2 infected cell proteins. Sera from fHSVΔpac DNA-immunized mice were pooled and analyzed for the presence of anti-HSV-1 and anti-HSV-2-specific antibodies by western immunoblot analysis of infected cells (lanes 1–3). Lanes 4–6 represent the autoradiographic images of the cell lysates shown in lanes 1–3. Radioactively labeled cell extracts were prepared, subjected to SDS-polyacrylamide electrophoresis, transferred to nitrocellulose, and immunostained as described in materials and methods. Lanes 1 and 4: lysates of cells infected with HSV-1 (strain F); lanes 2 and 5: mock infected cells (M); lanes 3 and 6: cells infected with HSV-2 (strain G). The numbers on the right of the figure refer to infected cell proteins (ICP) specified by HSV-1 (see, Morse, L. S., et al., *J. Virol.* 26:389–410 (1978)). The arrows point to the major capsid proteins (c) of both HSV-1 (ICP5) and HSV-2, or to clusters of immunologically stained HSV-1-specific proteins. The asterisk indicates a band, which was stained in the infected as well as in the mock infected cell lysates.

HSV-1-specific antibodies of the IgG2a and IgG2b isotypes were detected in the sera after priming with DNA or virus. Ten days after a second immunization with fHSVΔpac DNA, the HSV-1-specific antibody titer increased 10-fold, whereas a second dose of DISC HSV-1 resulted only in a 2- to 3-fold increase. This increase in the titer of HSV-1-specific antibodies upon second immunizations with fHSVΔpac or DISC HSV-1 indicates an induction of immune memory. Neutralizing antibodies were detected in sera of mice immunized twice with fHSVΔpac DNA or once with DISC HSV-1 (Table 3). A second immunization with DISC HSV-1 increased with the titer 8-fold. Serum from fHSVΔpac-immunized mice recognized a wide range of HSV-1-specific proteins, as determined by Western immunoblot analysis of cells infected with either HSV-1 or HSV-2 (FIG. 10). One of the proteins detected in both HSV-1 and HSV-2 infected cells represents the major capsid protein (ICP5).

Immunization of mice of a different strain, 129Sv/Ev, which is MHC compatible to C57BL/6, also resulted in the production of HSV-1-specific antibodies of all IgG isotypes upon two immunizations with fHSVΔpac or a single immunization with DISC HSV-1. Interestingly, a second immunization with DISC HSV-1 did not increase the antibody titer in these mice. Preliminary data indicate that following three immunizations with fHSVΔpac, the antibody titer is maintained for more than three months without further boosting the mice.

Immunization with fJHSVΔpac DNA Protects Mice from Lethal HSV-1 Infection

Figure 11A:
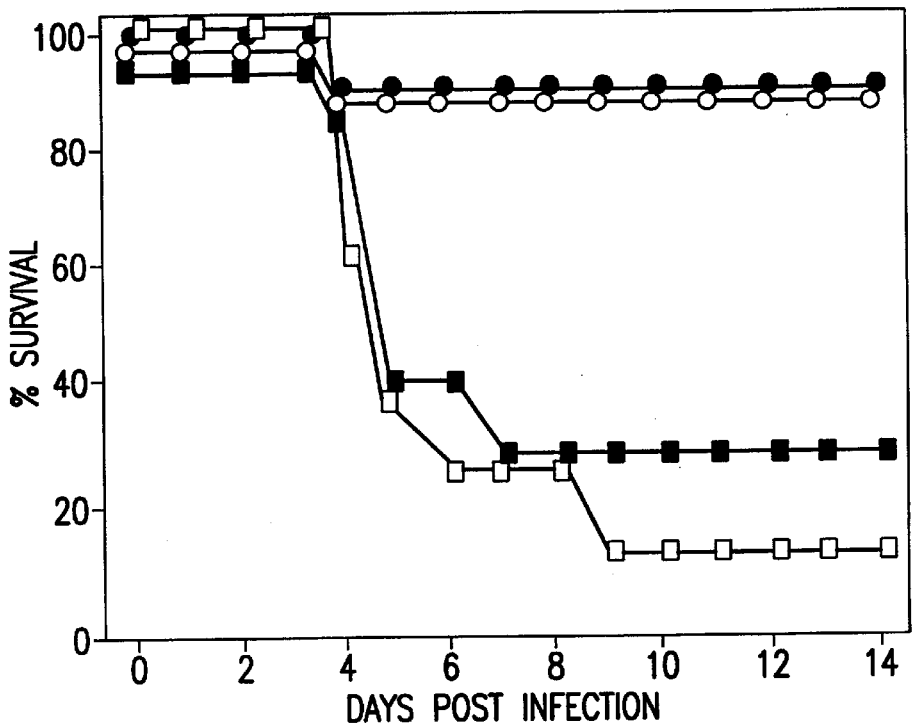
FIGS. 11A–11B depict graphs showing survival of mice following lethal challenge with wt HSV-1.

Next, it was determined whether the immune responses induced by immunization with fHSVΔpac DNA were protective against lethal HSV-1 infection. The i.c. route was chosen for the challenge experiments because mice are relatively resistant to HSV-1 infections by peripheral routes but highly susceptible to i.c. inoculation (Meignier, B., et al., *Virology* 162:251–254 (1988); Lewandowski, G., *Brain Behav Immun* 11:264–272 (1997); Grob, P., et al., *J Virol*, in press, (1999)). Ten days after a second immunization, groups of eight mice were challenged i.c. with $2\times10^5$ PFU (200 LD$_{50}$) of wt HSV-1. The results show clear protection of fHSVΔpac-immunized and DISC HSV-1-immunized mice, but not of control animals. Seven of eight mice immunized with fHSVΔpac DNA or DISC HSV-1 survived the challenge without showing any signs of disease. Animals that were immunized with a single dose of fHSVΔpac DNA or with control DNA were not protected and showed signs of disease including incoordination, ragged fur, and hunched position. Seven of the eight animals died within 9 days (FIG. 11A). These data indicate that immunization with fHSVΔpac DNA (twice 1.5 μg) confers protective immunity as effectively as infection with DISC HSV-1 (twice $10^9$ PFU). Of note, $10^9$ PFU of the DISC HSV-1 vaccine was chosen for the protection experiments because the CTL activity was comparable to that induced by 1.5 μg of fHSVΔpac DNA (FIGS. 8A and 8B).

Serum transfer experiments were performed to determine whether the humoral arm of the immune system was suffi-

TABLE 3

| | | | Serology | | | | |
|---|---|---|---|---|---|---|---|
| | Mouse | No. of | IgG isotype | | | | Neutraliza- |
| Immunogen | Strain | Immunizations | IgG1 | IgG2a | IgG2b | IgG3 | tion |
| fHSV pac | | | | | | | |
| DNA | C57BL/6 | 1 | 0.1 | 0.2 | 1.5 | <0.1 | <2 |
| | | 2 | 0.5 | 2.5 | 12.1 | 1 | 8 |
| | 129Sv/Ev | 1 | 0.1 | <0.1 | <0.1 | <0.1 | n.d. |
| | | 2 | 2.5 | 0.5 | 0.5 | <0.1 | n.d. |
| | | 3 | 6.7 | 12.4 | 2.5 | 0.5 | 8 |
| DISC | | | | | | | |
| HSV-1 | C57BL/6 | 1 | 2.5 | 11.1 | 32.5 | 1 | 8 |
| | | 2 | 1.6 | 12.5 | 61.3 | 2.5 | 64 |
| | 129Sv/Ev | 1 | 1.5 | 14.1 | 16.7 | 2.1 | n.d. |
| | | 2 | 3.2 | 18.5 | 11.3 | 8.3 | n.d. |
| | | 3 | 2.2 | 16.5 | 33.1 | 3.2 | 64 |

Figure 11B:
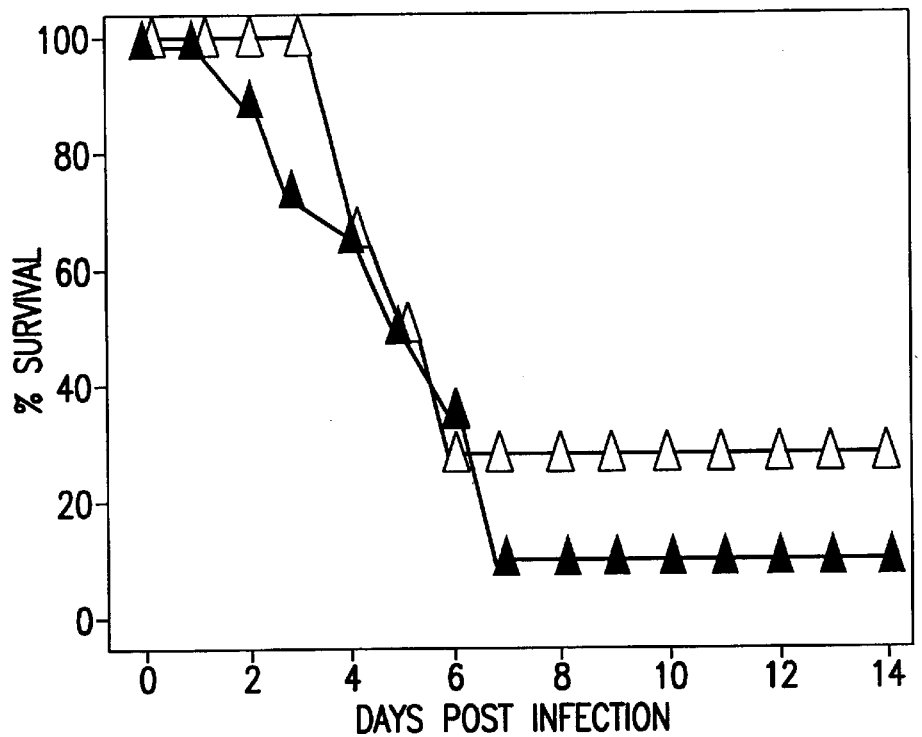

Groups of four mice were immunized with either 1.5 μg fHSV pac DNA by gold-particle bombardment or $10^3$ PFU of DISC HSV-1 by infection. Mice were boosted at biweekly intervals, and blood was collected immediately before boosting. Sera was analyzed for different IgG isotypes by ELISA (the mean titer is given as serum dilution × $10^{-3}$) or for the capacity to neutralize HSV-1 (titer = 1/serum dilution); n.d., not done.

cient to protect mice from lethal i.c. HSV-1 infection. Mice were intravenously inoculated with 100 μl of pooled sera from fHSVΔpac DNA-immunized or DISC HSV-1-immunized mice, which had a neutralization titer of 32. Post-transfer serum collected 4 hours later had a neutralization titer of 16. The animals (eight mice per group) challenged 4 hours after serum transfer by i.c. infection with $2 \times 10^5$ PFU of wt HSV-1 showed signs of disease within a few days, and only 3 of the 16 mice survived longer than 7 days (FIG. 11B). Furthermore, all four animals injected intraperitoneally with 1 ml of immune-serum with a neutralization titer of 64 died within 7 days after i.c. challenge with $2 \times 10^5$ PFU of wt HSV-1. These data are consistent with previous results, which had established that cellular immune responses are required to clear infectious HSV-1 from the brain (Lewandowski, G., *Brain Behav Immun* 11:264–272 (1997)).

Discussion

The prototype "BAC-VAC" described in this Example contains a 150-kb, modified HSV-1 genome which is replication-competent in mammalian cells and expresses at least all of the ~36 viral genes that are essential for HSV-1 replication, but does not produce infectious progeny virus (fHSVΔpac; Saeki, Y., et al., *Hum Gene Ther* 9:2787–2794 (1998) and Example 1). Although the pac sequence is deleted in fHSVΔpac, deleting other essential herpes sequences (i.e., ICP27) in lieu of pac, or in combination with pac, are alternative embodiments.

Immunization with fHSVΔpac DNA induced broad cellular and humoral immune responses and protected the animals from lethal HSV-1 infection as effectively as vaccination with an equivalent amount of a modified live virus (DISC HSV-1). The results also show that the humoral immune responses induced by fHSVΔpac or DISC HSV-1 were not sufficient to confer protection against the lethal challenge. It will be important to determine whether immunization with fHSVΔpac DNA has an influence on the capability of wt HSV-1 to establish latency after experimental infections via eye, ear, or footpad.

The focus of this study was to demonstrate the usefulness of BACs to carry large, antigen-encoding DNA fragments, such as modified viral genomes. Similar strategies, however, could be established on other large capacity shuttle vectors, such as yeast artificial chromosomes (YAC-VAC), P1-derived artificial chromosomes (PAC-VAC), or cosmids (COS-VAC). BAC-VAC combines the high immunogenicity of modified live virus vaccines with the safety and simplicity of DNA vaccines. Moreover, as opposed to live virus vaccines, the *E. coli* propagated BAC-VAC can easily and extensively be modified to (i) study the complex interactions between host and parasite; (ii) eliminate specific components of the target pathogen to increase safety and/or counter the capability to evade detection and elimination by the host's immune system; (iii) combine heterologous genetic elements, such as antigen-encoding DNA and sequences that support replicative amplification, to enhance or manipulate the immune response; and (iv) develop novel vaccination strategies against many different target agents, including viruses, bacteria, parasites, and tumors.

Although the foregoing invention has been described in some detail by way of illustration and example for purposes of clarity of understanding, this invention is not limited to the particular embodiments disclosed, but is intended to cover all changes and modifications that are within the spirit and scope of the invention as defined by the appended claims.

All publications and patents mentioned in this specification are indicative of the level of skill of those skilled in the art to which this invention pertains. All publications and patents are herein incorporated by reference to the same extent as if each individual publication or patent application were specifically and individually indicated to be incorporated by reference.

What is claimed is:

1. A system for packaging herpes virus amplicon vectors into infectious particles, said system comprising:
   (a) a herpes virus amplicon vector; and
   (b) a packaging vector comprising a single cloning vehicle containing a herpes virus genome with an intact cleavage/packaging site-containing sequence (pac site), wherein said packaging vector is replication proficient but packaging defective, and the size of said packaging vector is greater than the size of a wild type herpes virus genome, thereby impairing the capsid's ability to close in order to generate infectious virus;
   wherein said herpes virus amplicon vector is packaged into infectious particles by cotransfection with said packaging vector, said packaging vector providing helper virus functions.

2. The herpes virus amplicon vector packaging system of claim 1, wherein said herpes virus genome contained in the packaging vector is a herpes simplex virus.

3. The herpes virus amplicon vector packaging system of claim 2, wherein said herpes simplex virus is HSV-1.

4. The herpes virus amplicon vector packaging system of claim 1, wherein said packaging vector of (b) is a large capacity cloning vector.

5. The herpes virus amplicon vector packaging system of claim 4, wherein said large capacity cloning vector is a bacterial artificial chromosome (BAC), cosmid, yeast artificial chromosome (YAC), PAC P1 phage-based vector, or viral-based vector.

6. The herpes virus amplicon vector packaging system of claim 5, wherein said large capacity cloning vector is a bacterial artificial chromosome (BAC).

7. The herpes virus amplicon vector packaging system of claim 1, wherein said packaging vector further comprises, in addition to the herpes virus genome, a viral, bacterial, or parasitic gene or genome.

8. The herpes virus amplicon vector packaging system of claim 1, wherein said amplicon vector of (a) is a plasmid or large capacity cloning vector.

9. The herpes virus amplicon vector packaging system of claim 8, wherein said amplicon vector is a large capacity cloning vector.

10. The herpes virus amplicon vector packaging system of claim 9, wherein said large capacity cloning vector is a bacterial artificial chromosome (BAC), cosmid, yeast artificial chromosome (YAC), PAC P1 phage-based vector, or viral-based vector.

11. The herpes virus amplicon vector packaging system of claim 10, wherein said large capacity cloning vector is a bacterial artificial chromosome (BAC).

12. The herpes virus amplicon vector packaging system of claim 1, wherein said amplicon vector contains a transgene cassette comprising one or more heterologous nucleotide sequence(s) of interest.

13. The herpes virus amplicon vector packaging system of claim 12, wherein said one or more heterologous nucleotide sequence(s) of interest in said amplicon vector encodes a therapeutic or antigenic protein(s).

14. The herpes virus amplicon vector packaging system of claim 13, wherein at least one of said heterologous nucleotide sequence(s) of interest in said amplicon vector encodes a therapeutic protein.

15. The herpes virus amplicon vector packaging system of claim 13, wherein at least one of said heterologous nucleotide sequence(s) of interest in said amplicon vector encodes an antigenic protein.

16. A method of generating recombinant herpes virus vectors, said method comprising cotransfecting a host cell with:
   (a) a herpes virus amplicon vector, and
   (b) a packaging vector comprising a single cloning vehicle containing a herpes virus genome with an intact cleavage/packaging site-containing sequence (pac site), wherein said packaging vector is replication proficient but packaging defective, and the size of said packaging vector is greater than the size of a wild type herpes virus genome, thereby impairing the capsid's ability to close in order to generate infectious virus.

17. The method of claim 16, wherein said herpes virus genome contained in said packaging vector is a herpes simplex virus.

18. The method of claim 17, wherein said herpes simplex virus is HSV-1.

19. The method of claim 16, wherein said packaging vector further comprises, in addition to the herpes virus genome, a viral, bacterial, or parasitic gene or genome.

20. The herpes virus amplicon packaging system of claim 1, wherein the possibility of recombination between said amplicon vector and said packaging vector is reduced by:
   (a) disrupting an essential gene in the packaging vector,
   (b) increasing the size of the single cloning vehicle,
   (c) providing different promoters in said amplicon vector and said packaging vector, or
   (d) providing different origins of DNA replication in said amplicon vector and said packaging vector.

21. The herpes virus amplicon packaging system of claim 20, wherein the possibility of recombination between said amplicon vector and said packaging vector is reduced by disrupting an essential gene in the packaging vector.

22. The herpes virus amplicon vector packaging system of claim 21, wherein said essential gene in the packaging vector that is disrupted is ICP27.

23. A method of inducing an immune response against a herpes virus in an animal, by administering to said animal in need of an immune response against a herpes virus, said recombinant herpes virus vectors generated by the method of claim 16.

24. A method of inducing an immune response against a herpes virus in an animal, by administering to said animal in need of an immune response against a herpes virus, said recombinant herpes virus vectors generated by the method of claim 17.

25. A method of inducing an immune response against HSV-1 in an animal, by administering to said animal in need of an immune response against HSV-1, said recombinant HSV-1 vectors generated by the method of claim 18.

26. A method of inducing an immune response against a viral, bacterial, or parasitic pathogen, in an animal, by administering to said animal in need of an immune response against said pathogen, said recombinant herpes virus vectors generated by the method of claim 19.

27. A system for packaging herpes virus amplicon vectors into infectious particles, said system comprising:
   (a) a herpes virus amplicon vector;
   (b) a packaging vector comprising a single cloning vehicle containing a herpes virus genome that lacks an intact cleavage/packaging site-containing sequence (pac site), wherein said packaging vector is replication proficient, and the size of said packaging vector is greater than the size of a wild type herpes virus genome, thereby impairing the capsid's ability to close in order to generate infectious virus;

wherein said herpes virus amplicon vector is packaged into infectious particles by cotransfection with said packaging vector, said packaging vector providing helper virus functions.

28. The herpes virus amplicon vector packaging system of claim 27, wherein an essential gene in said packaging vector is disrupted or deleted.

29. The herpes virus amplicon vector packaging system of claim 28, wherein said essential gene in said packaging vector that is disrupted or deleted is ICP27.

* * * * *